(12) United States Patent
Fujiwara et al.

(10) Patent No.: US 7,974,671 B2
(45) Date of Patent: Jul. 5, 2011

(54) LIVING BODY INFORMATION SIGNAL PROCESSING SYSTEM COMBINING LIVING BODY OPTICAL MEASUREMENT APPARATUS AND BRAIN WAVE MEASUREMENT APPARATUS AND PROBE DEVICE USED FOR THE SAME

(75) Inventors: Michiyuki Fujiwara, Kashiwa (JP); Tsuneaki Kawaguchi, Shounan-machi (JP); Fumio Kawaguchi, Hinode-machi (JP); Shingo Kawasaki, Matsudo (JP); Atsushi Maki, Saitama (JP); Yukiko Hirabayashi, Saitama (JP); Yukari Yamamoto, Saitama (JP); Masashi Kiguchi, Saitama (JP); Hiroki Sato, Saitama (JP); Tsuyoshi Yamamoto, Saitama (JP); Takushige Katsura, Saitama (JP); Hideo Kawaguchi, Saitama (JP)

(73) Assignees: Hitachi Medical Corporation, Tokyo (JP); Hitachi, Ltd., Tokyo (JP)

( * ) Notice: Subject to any disclaimer, the term of this patent is extended or adjusted under 35 U.S.C. 154(b) by 1456 days.

(21) Appl. No.: 10/572,357

(22) PCT Filed: Sep. 3, 2004

(86) PCT No.: PCT/JP2004/012856
§ 371 (c)(1),
(2), (4) Date: Mar. 16, 2006

(87) PCT Pub. No.: WO2005/034761
PCT Pub. Date: Apr. 21, 2005

(65) Prior Publication Data
US 2007/0083097 A1    Apr. 12, 2007

(30) Foreign Application Priority Data

Sep. 19, 2003  (JP) ................................ 2003-327354
Sep. 19, 2003  (JP) ................................ 2003-328573
Sep. 19, 2003  (JP) ................................ 2003-328702

(51) Int. Cl.
*A61B 5/00* (2006.01)

(52) U.S. Cl. ........ 600/344; 600/310; 600/340; 600/407; 600/409; 600/473; 600/544

(58) Field of Classification Search .................. 600/310, 600/340, 344, 407, 409, 473, 544
See application file for complete search history.

(56) References Cited

U.S. PATENT DOCUMENTS 5,119,815 A * 6/1992 Chance ......................... 600/433
(Continued)

FOREIGN PATENT DOCUMENTS

JP      09-098972     4/1997
(Continued)

*Primary Examiner* — Tse Chen
*Assistant Examiner* — Baisakhi Roy
(74) *Attorney, Agent, or Firm* — Antonelli, Terry, Stout & Kraus, LLP.

(57) ABSTRACT

A living body information signal processing system (100) combining organically a living body optical measurement apparatus and a brain wave measurement apparatus, the living body optical measurement apparatus (300) in which inspection light of from visible to near infrared is irradiated on a head portion of a subject (140) and the penetration light is received and which measures an optical characteristic variation induced by a brain activity inside the head portion as a living body optical signal and the brain wave measurement apparatus (400) which measures an electrical characteristic variation induced by a brain activity inside the head portion of the subject as a brain wave signal, is provided with a probe device (50) used for both apparatus; and a living body information signal processing and displaying device (200) which displays the living body optical signal corresponding to respective measurement positions from the living body optical measurement apparatus and the brain wave signal corresponding to respective measurement positions from the brain wave measurement apparatus on a common display device while correlating the respective measurement positions each other, thereby, with the system comprehensive observation of both data can be achieved.

16 Claims, 18 Drawing Sheets

U.S. PATENT DOCUMENTS

| | | | | |
|---|---|---|---|---|
| 5,803,909 | A * | 9/1998 | Maki et al. | 600/310 |
| 5,853,370 | A * | 12/1998 | Chance et al. | 600/473 |
| 6,240,309 | B1 * | 5/2001 | Yamashita et al. | 600/407 |
| 6,611,698 | B1 * | 8/2003 | Yamashita et al. | 600/310 |
| 6,640,133 | B2 * | 10/2003 | Yamashita et al. | 600/476 |
| 7,039,454 | B1 * | 5/2006 | Kaga et al. | 600/476 |
| 7,142,906 | B2 * | 11/2006 | Yamashita et al. | 600/476 |
| 7,150,717 | B2 * | 12/2006 | Katura et al. | 600/504 |

FOREIGN PATENT DOCUMENTS

| | | |
|---|---|---|
| JP | 09-149903 | 6/1997 |
| JP | 2000-237194 | 9/2000 |
| JP | 2001-340312 | 12/2001 |
| JP | 2002-177281 | 6/2002 |
| JP | 2002-360538 | 12/2002 |
| JP | 2003-144437 | 5/2003 |
| JP | 2003-149137 | 5/2003 |

* cited by examiner

FIG. 6
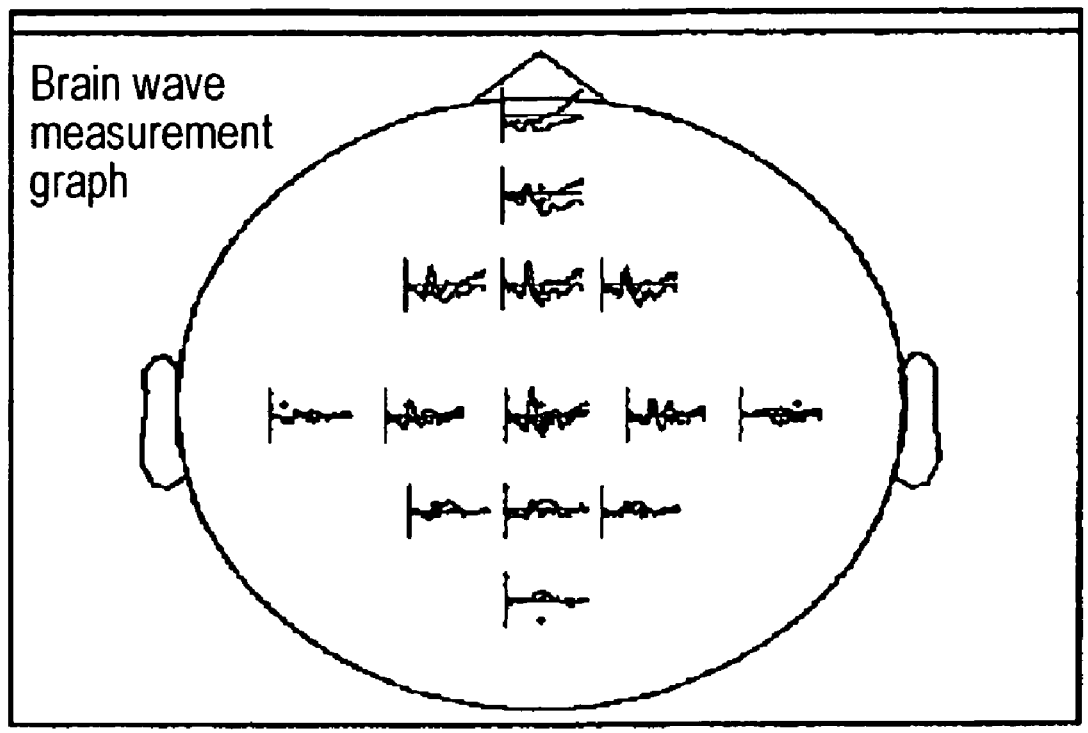
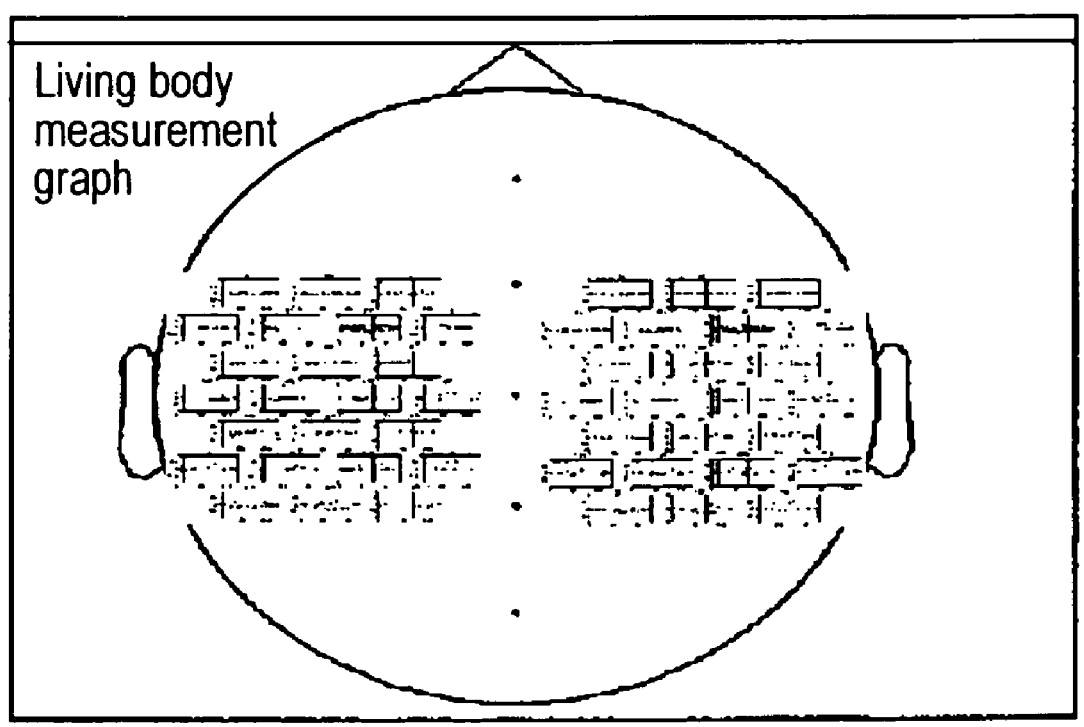

FIG. 7

(a) Spatial distribution of optical measurement signal (b) Spatial distribution of brain wave measurement signal

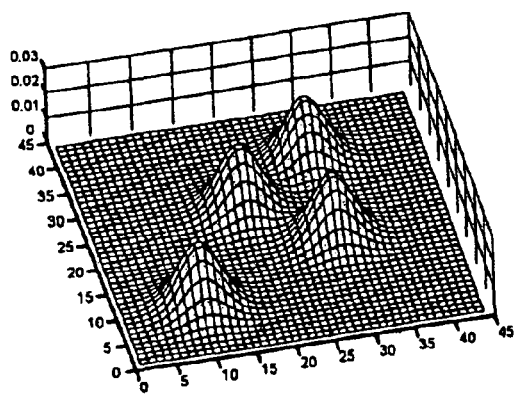
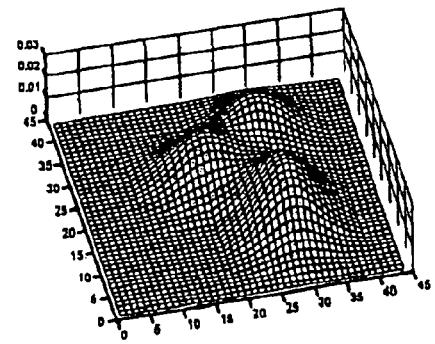

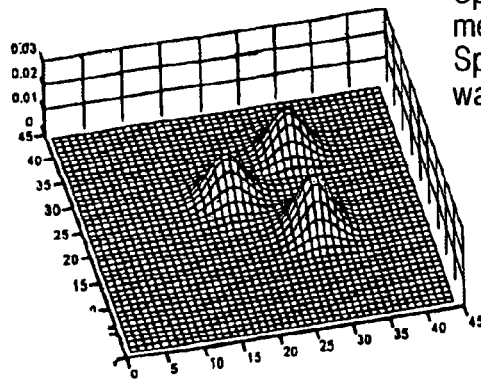

(c) Spatial distribution of optical measurement signal × Spatial distribution of brain wave measurement signal

FIG. 8

(a) Brain wave measurement signal intensity

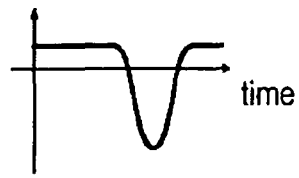
time (b) Optical measurement signal intensity

time (c) Optical measurement signal intensity

Negative correlation

Phase difference

Brain wave measurement signal intensity

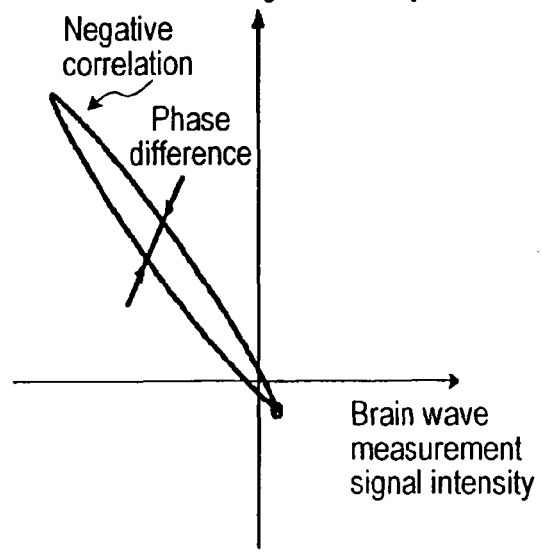

|  | Brain wave measurement (ERP) | Optical measurement |
|---|---|---|
| Standard sampling period (Stimulation interval) | Only initial component : 0.1s<br>Only last component : 0.5-1s | Period of 15~30 s |
| Sampling times | 20~200 times | 5~10 times |

LIVING BODY INFORMATION SIGNAL PROCESSING SYSTEM COMBINING LIVING BODY OPTICAL MEASUREMENT APPARATUS AND BRAIN WAVE MEASUREMENT APPARATUS AND PROBE DEVICE USED FOR THE SAME

FIELD OF THE INVENTION

The present invention relates to a living body information signal processing system combining a living body optical measurement apparatus and a brain wave measurement apparatus and a probe device used for the same, which, in particular, permits displaying a measurement result of living body optical signals and brain wave signals on a common display device and permits a highly accurate living body optical measurement eliminating ineffective measurement by making use of the measured brain wave signal data, and relates to a probe device used for the living body optical measurement apparatus and the brain wave measurement apparatus which permits easy attachment thereof for quickening a preparation work for the measurement.

CONVENTIONAL ART

A living body optical measurement apparatus is an apparatus which irradiates light having wavelengths of from visible to near infrared region onto a living body subject, measures penetration light passed through the intra living body while repeating random scattering and images optical characteristic differences in the intra living body. With such living body optical measurement apparatus, through measuring living body metabolites such as hemoglobin and blood stream, since living body functions can be measured conveniently with a low restriction to the living body and in a non-invasive manner to the living body, the application of the living body optical measurement apparatus is spreading in the field of such as clinical medicine and brain science.

An activation of higher brain functions relating to, for example, thinking, language, sense and motor is closely related to oxygen metabolism and blood circulation in the intra living body and corresponds to concentration variation of specific pigments (such as hemoglobin) in the intra living body. Accordingly, for example, JP-A-9-149903 discloses an apparatus which irradiates light of plurality of wavelengths of from visible to infrared region which are likely absorbed by the specific pigments onto a plurality of portions of a brain, detects penetration light passed through the intra brain from a plurality of portions and images from the absorbed light amount variations of such as metabolites concentration and hemoglobin concentration in blood in the intra brain, and permits measurement of higher brain functions.

As clinical applications of the living body optical measurement apparatus, when, for example, head is selected as the measurement object, measurements of such as states of activation and variation of hemoglobin in the intra brain and local bleeding in the intra brain are enumerated.

On the other hand, brain wave signals which are generated from the living body in association with the like brain function activity are being used from the past for diagnosing brain diseases as a mean which can directly measure activities of the brain nerves. Namely, in the field of brain science brain waves which are generated in association with the brain activity are measured by contacting electrodes on the scalp and based on brain wave signals (such as $\alpha$ wave, $\beta$ wave, $\theta$ wave and $\delta$ wave) in a specific frequency band region an analysis of higher brain functions such as intelligent function such as thinking and language and motor function has been attempted. For example, a research and development is advanced in which by contacting many electrodes on the surface of the scalp, a two dimensional electroencephalogram is obtained, functions of respective portions in the brain are analyzed and existence and absence of such as brain disorder is diagnosed for reflecting the same to medical treatment.

Although the physical amounts of the measurement object are different, since both signals relate to the same brain activity, the information carried on the signals is different, and further, their spatial and temporal characteristics are in a complementary relationship, simultaneous measurement of the both signals has been attempted.

Although the above referred to simultaneous measurement of the brain wave signals and the living body optical signals is by itself comparatively easy because of no physical interference between both signals, however, since the temporal and spatial characteristics of both signals differ greatly, it was difficult even for a specialist doctor to observe both signals comprehensively and to apply the observation result to disease diagnosis.

In particular, only with the simultaneous measurement and simultaneous display of both signals according to the conventional manner as disclosed, for example, in JP-A-2003-149137, an effective diagnosis information could not be obtained efficiently.

Now, when measuring the higher brain functions such as thinking, language and motor with the conventional living body optical measurement apparatus, stimulation is given to the brain through such as the ear sense and eyesight, the state variation of the brain before and after the stimulation is imaged and both images are compared to diagnose the brain function.

Although the analysis of the relationship between the brain state appeared on the optical measurement image and the stimulation given is advancing, a correct diagnosis is not yet achieved based on the optical measurement image while correlating with the brain state determined by the brain wave measurement apparatus.

Further, when performing the living body optical measurement and the brain wave measurement simultaneously, it is necessary to dispose top end portions of a plurality of irradiation use optical fibers and light receiving use optical fibers carried by a living body optical measurement apparatus use probe device on predetermined positions of the head while pushing out hair disturbing the measurement for every optical fibers and subsequently to dispose tops of a plurality of brain wave electrodes carried by the brain wave measurement apparatus use probe device while avoiding the previously disposed optical fiber positions, therefore, it takes great many time and work for preparation and setting before starting the measurement.

An object of the present invention is to provide a living body information signal processing system combining a living body optical measurement apparatus and a brain wave measurement apparatus which permits an observer to easily understand living body optical signals and brain wave signals, to facilitate comprehensive observation of both signals and to provide new diagnostic information which can not be obtained from the individual signals.

Another object of the present invention is to provide a living body information signal processing system combining a living body optical measurement apparatus and a brain wave measurement apparatus which permits a highly accurate living body optical measurement eliminating ineffective measurement by making use of the brain wave signal data measured by the brain wave measurement apparatus.

A still another object of the present invention is to provide a probe device used for a living body optical measurement apparatus and a brain wave measurement apparatus which is adapted for both living body optical measurement and brain wave measurement and reduces time and work required for the measurement setting.

SUMMARY OF THE INVENTION

One aspect of the present invention is directed to a living body information signal processing system combining organically a living body optical measurement apparatus and a brain wave measurement apparatus in which living body optical signals and brain wave signals measured respectively by the living body optical measurement apparatus and the brain wave measurement apparatus are displayed on a common display device while correlating to the respective measurement positions so as to permit comprehensible observation of both signals.

Another aspect of the present invention is directed to a living body information signal processing system combining organically a living body optical measurement apparatus and a brain wave measurement apparatus, which permits to obtain living body optical signal data corresponding to a predetermined brain state, for example, an awaking state represented by brain wave signal data measured by the brain wave measurement apparatus.

Still another aspect of the present invention is directed to a probe device for the above system which is provided with a common holder which is mounted on a subject, irradiation use optical fibers which are attached to the holder and irradiate inspection light used for the living body optical measurement, light receiving use optical fibers which are attached to the holder with an interval with respect to the irradiation use optical fibers and receive penetration light of the inspection light from the subject and electroencephalogram electrodes which are attached at intermediates between the irradiation use optical fibers and light receiving use optical fibers and are to be contacted to the subject.

BRIEF DESCRIPTION OF THE DRAWINGS

FIG. 6 is a still further display example displayed on a display device by a living body signal processing and displaying device in the living body signal processing system according to the present invention, in which on one of two images displayed in parallel both showing a head portion of a subject, time course graphs of the brain wave measurement signals are shown on respective corresponding measurement positions and on the other image, time course graphs of the living body optical measurement signals are shown on respective corresponding measurement positions.

FIG. 7 is a still further display example displayed on a display device by a living body signal processing and displaying device in the living body signal processing system according to the present invention, in which (a) displays a spatial distribution of optical measurement signals, (b) displays a spatial distribution of brain wave measurement signals in a same measurement space and (c) displays the product spatial distribution of the spatial distributions of (a) and (b).

FIG. 8 is a diagram for explaining a computation for determining correlation between brain wave measurement signals and optical measurement signals at a certain measurement position by a living body signal processing and displaying device in the living body signal processing system according to the present invention, in which (a) shows a time course graph along time axis of intensity of brain wave measurement signals normalized by the maximum value, (b) shows a time course graph along the same time axis of intensities of optical measurement signals normalized by the maximum value and (c) shows a diagram formed by plotting intensities of the brain wave measurement signals and the optical measurement signals one of which is on one of two perpendicularly crossing axes and the other on the other axis while using time as a parameter.

DETAILED DESCRIPTION OF THE EMBODIMENT

Herein below, preferred embodiments of the living body information signal processing system according to the present invention will be explained in detail with reference to the drawings attached.

Figure 1:
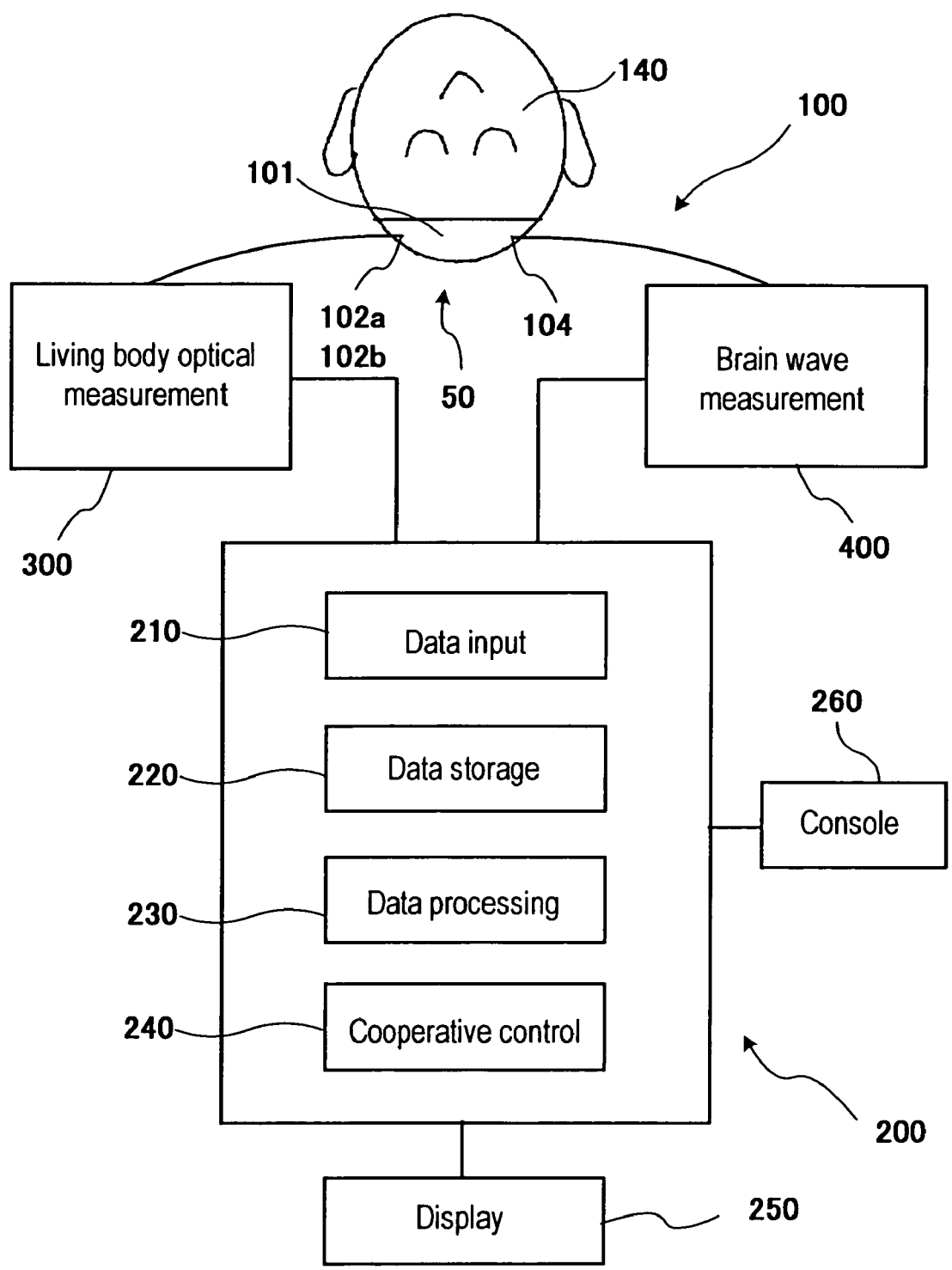
FIG. 1 is a block diagram showing schematically an embodiment of a living body information signal processing system combining a living body optical measurement apparatus and a brain wave measurement apparatus according to the present invention.

FIG. 1 shows a constitution of the living body information signal processing system 100 according to an embodiment of the present invention. The living body information signal processing system 100 is constituted by a living body optical measurement apparatus 300, a brain wave measuring apparatus 400 and a living body signal processing and displaying device 200 which processes input signals from both and displays the processed results.

A probe device 50 for the living body optical measurement apparatus 300 and the brain wave measuring apparatus 400 is mounted on a head portion of a subject 140 and the probe device 50 used for the system of the present invention is constituted by a plurality of inspection light irradiation use optical fibers 102a and penetration light receiving use optical fibers 102b for the living body optical measurement apparatus 300 and a plurality of brain wave electrodes 104 and a common rubber made or plastic made probe holder 101 for holding these fibers and electrodes at predetermined positions.

The living body signal processing and displaying device 200 is constituted by a data input unit 210, a data storage unit 220, a data processing unit 230, a cooperative control unit 240, a display device 250 and a console 260.

Time variation signals of hemoglobin of the subject, which are measured by the living body optical measurement apparatus 300 are input in the data input unit 210 and transferred to the data storage unit 220 to store the same. Information showing positions of respective measurement points and information of measurement time are added to the data and are transferred at the same time.

On the other hand, variation of brain wave signals from the electrodes disposed at the head portion of the same subject, which are measured by the brain wave measuring apparatus 400 are also input in the data input unit 210 together with information showing measurement time and respective measurement points and transferred to the data storage unit 220 to store the same.

The data processing unit 230 performs a comprehensive processing based on the data from the two apparatus and the added information of the measurement time and the measurement positions and the processed result is displayed on the display device 250.

The data display is performed either in real time during the measurement or in off line after the measurement, however, display methods which will be explained herein below are applicable for both cases.

Further, other than the real time and off line display of both data, by means of combination of different time modes in which only one data of living body optical signals and brain wave signals is displayed in real time and the other data is displayed from the data stored, an observation of real time measurement can be facilitated.

Since the living body signals and the brain wave signals are signals at a plurality of measurement points on the scalp, the information showing the measurement position is stored. Display manners of the respective signals are, for example, as follows;

1. Time course graphs showing time variation of signals at respective points,
2. Time course maps in which the time course graphs of above 1 are distributed to the respective measurement positions,
3. Two dimensional images constituted by averaging the measurement signals at respective points at a specific time or at a specific time band,
4. Animating images of the two dimensional image of above 3 prepared by the signals at the respective points and at the specific time.

In the living body information signal processing system 100, when combining the above display manners properly depending on the purpose of an observer, a comprehensive observation of the living body signals and the brain wave signals can be achieved easily.

The brain wave measurement apparatus 400, after mounting the brain wave electrodes at predetermined portions of the head portion of the subject and observing currents led from the electrodes, can catch nerve activity in the brain as specific signals of respective points in the brain. The brain wave signals include induction brain waves which are obtained by measuring a quick reaction of 10-300 ms in response to repeating stimulations of many times, and continuous brain waves which are obtained by measuring the brain waves continuously according to time, and measurement methods and measurement devices suitable for the respective measurements have been developed and used widely for clinical applications.

In connection with signals measured by the living body optical measurement apparatus 300 and the brain wave measuring apparatus 400, a variation of hemoglobin amount at respective measurement points according to time variation with regard to living body optical signals and a variation of electrical signals at respective time with regard to brain signals, in that a potential variation in time direction during stimulation repeating period with regard to the induction method and primarily an oscillating variation of electrical signals over the entire measurement time range with regard to the continuation method are recorded and stored.

Both signals are stored being added of information of ID of the subject and others and information with regard to measurement positions and measurement time.

Herein below, sequences of displaying at the same time or while shifting time each other information of living body optical signals and brain wave signals in a convenient manner and in a manner that an observer can easily diagnose will be explained with reference to specific examples.

Figure 2:
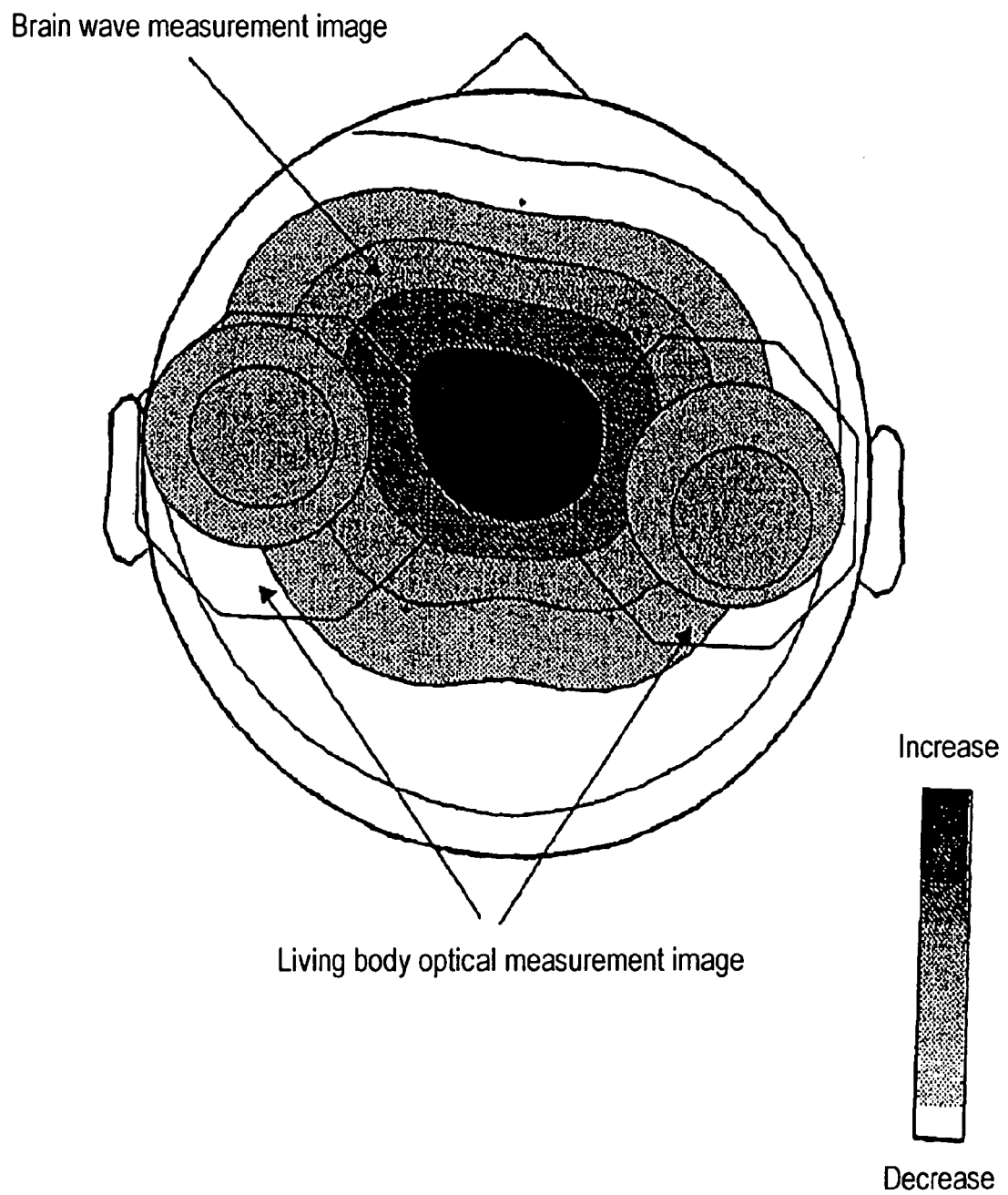
FIG. 2 is a display example displayed on a display device by a living body signal processing and displaying device in the living body signal processing system according to the present invention, in which on a two dimensional brain wave measurement image which is superposed on an image showing a head portion of a subject, a two dimensional living body optical measurement image is further superposed.

In FIG. 2, among measured signals, a two dimensional image obtained by the brain wave measurement is at first displayed while superposing on an image showing a head portion of the subject and further, a two dimensional image of the living body optical measurement is displayed by superposing on the two dimensional image of the brain wave measurement. At this instance, the two dimensional image of the living body optical measurement is displayed in a different hue from that of the two dimensional image of the brain wave measurement. For the two dimensional image display as in the present example, although a pseudo light and shade formed by mixing specific colors of more than one is usually used other than the use of monochromatic light and shade, in the present example, in order to ease discrimination of both two dimensional images, different pseudo colors, for example, red-blue hue for the former and yellow-green hue for the latter are used.

Further, the two dimensional image of the brain wave measurement is displayed in a pseudo color light and shade, and the living body optical signals are displayed in a contour diagram using color lines not contained in the pseudo color and superposed on the two dimensional image.

The up and down relationship of both display layers above can be inverted, further, the up and down relationship can be designed to be able to arbitrarily designate depending on desire of the observer. Still further, when one of the two layer images is displayed in semi-transparent, the relationship of both can be easily observed.

Figure 3:
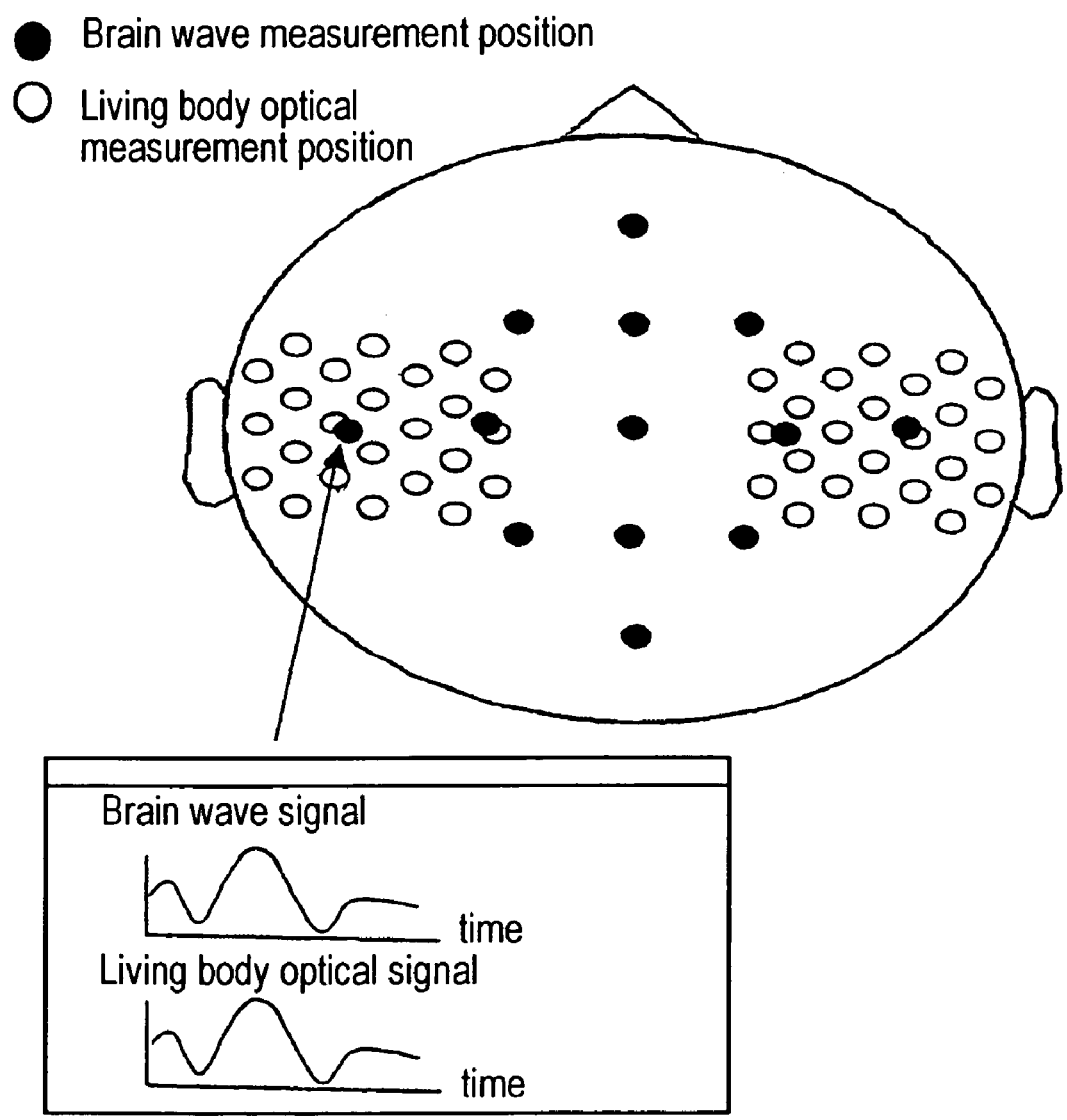
FIG. 3 is another display example displayed on a display device by a living body signal processing and displaying device in the living body signal processing system according to the present invention, in which a two dimensional image showing measurement positions of brain wave signals and living body optical signals superposed on an image showing a head portion of a subject and a selected position shown by an arrowed led out line and variations of brain wave signals and living body optical signals at the selected position shown in parallel along time axis, are displayed.

FIG. 3 shows an example of led out screen image in which when a desired observation position is selected via the console 260 from the two dimensional image showing measurement positions of the brain wave signals and the living body optical signals, two kinds of time course data diagrams of the brain wave signals and the living body optical signals are displayed in parallel on an area different from the position displaying image on the display screen together with an arrowed mark showing the selected position.

Figure 4:
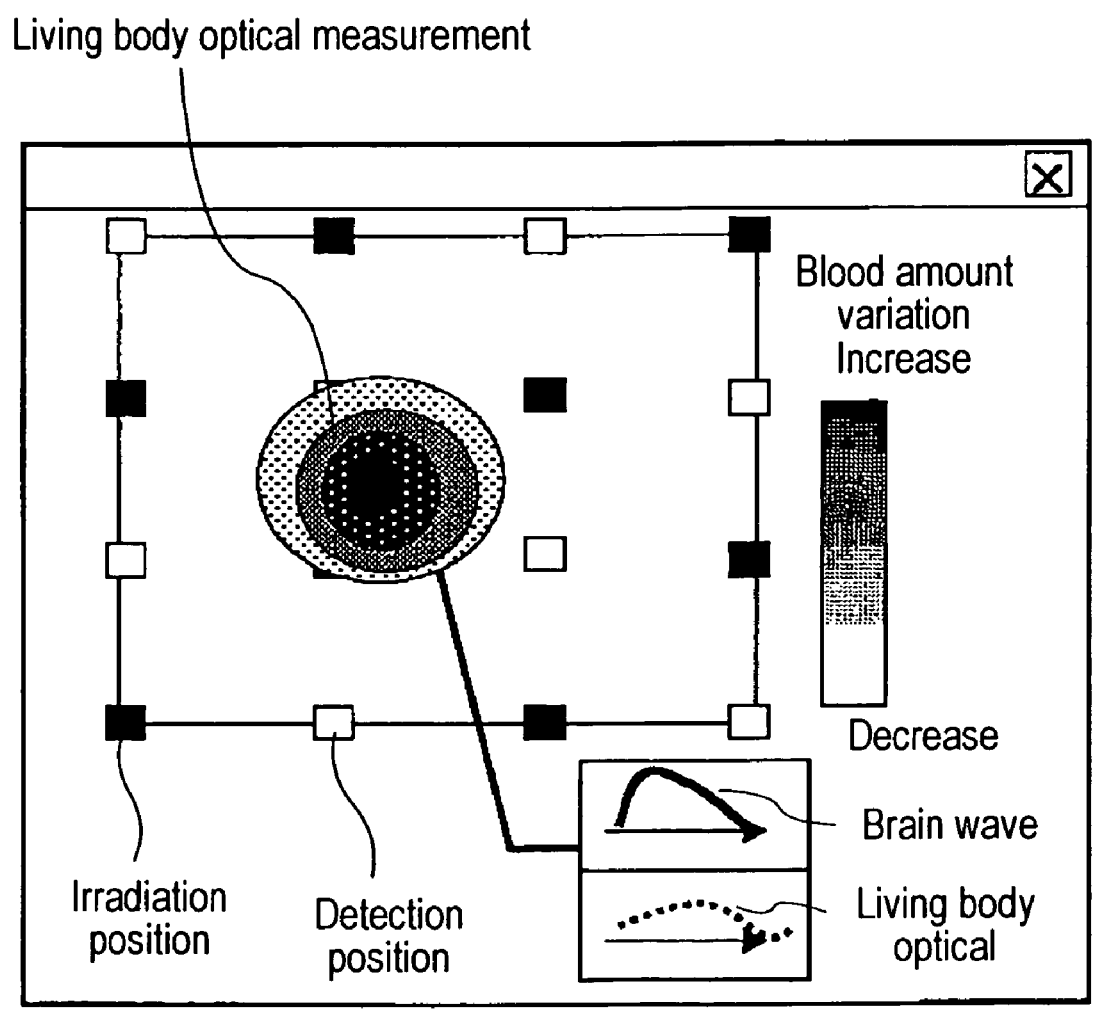
FIG. 4 is still another display example displayed on a display device by a living body signal processing and displaying device in the living body signal processing system according to the present invention, in which a two dimensional living body optical measurement image is displayed while being superposed on a two dimensional image showing light irradiation positions and penetration light detection portions thereof on the subject and a selected position shown by an arrowed led out line and variations of brain wave signals and living body optical signals at the selected position shown in parallel along time axis, are displayed.

In FIG. 4, the above led out screen image is displayed on the two dimensional measurement position image and together with the two dimensional distribution image, a time variation relationship of two signals of the living body penetration light and the brain wave at a certain specific measurement point is conveniently displayed. The two signals of the living body penetration light and the brain wave are measured at the same timing at the same measurement position and display a time variation relationship of the two signals. The brain wave graph and the living body penetration light graph shown in parallel in FIG. 4 are respectively those measured at the same timing, with which how the graphs of the brain wave and the living body penetration light vary according to time can be grasped. Further, the above measurement point can be arbitrarily set via the console.

Further, when the brain wave is measured and the living body penetration light is not measured, only the time variation of the brain signals can be displayed, and when the living body penetration light is measured and the brain wave is not measured, only the time variation of the living body optical signal can be displayed.

Figure 5:
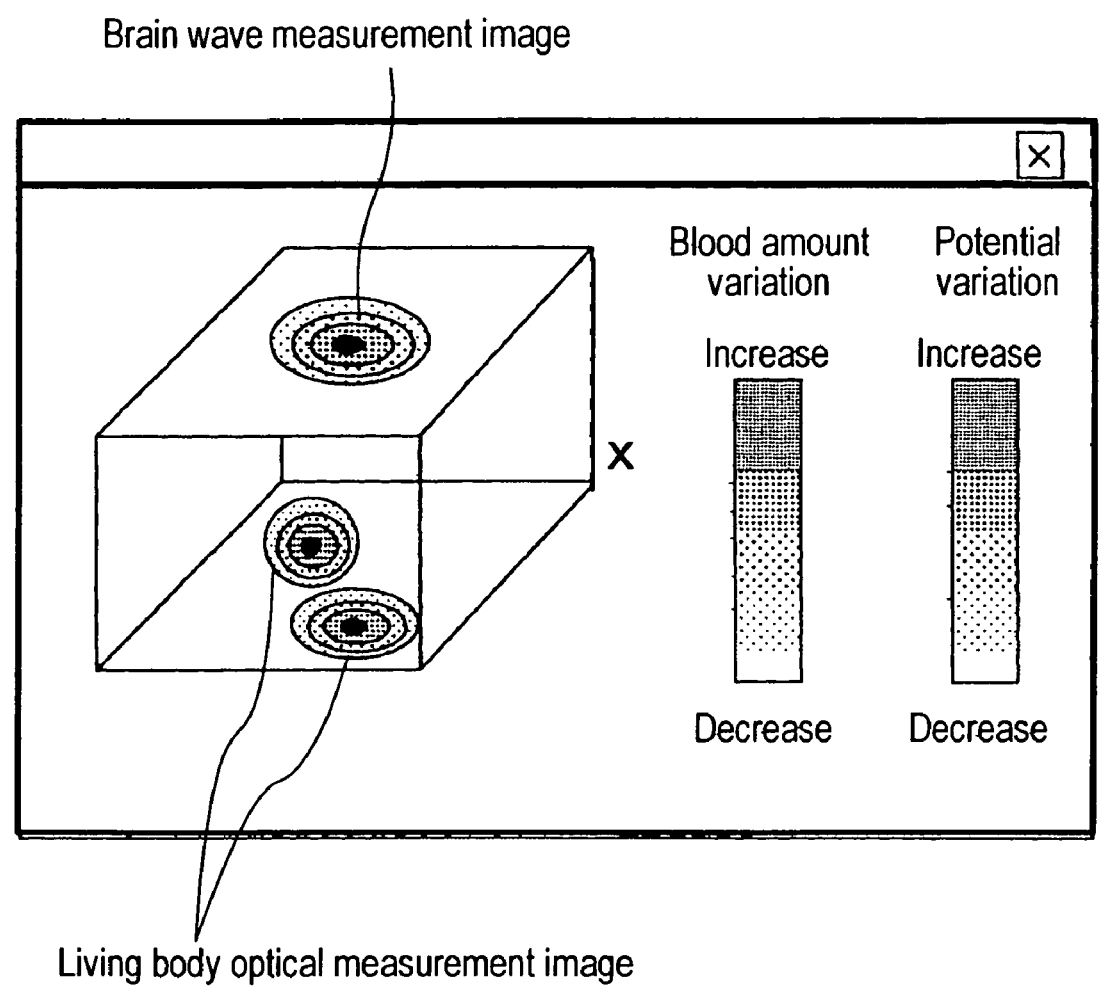
FIG. 5 is a further display example displayed on a display device by a living body signal processing and displaying device in the living body signal processing system according to the present invention, in which the up and down relationship of the two dimensional brain wave measurement image and the two dimensional living body optical measurement image as shown in FIG. 2 are inverted and the former is projected on a first layer and the latter is projected on a second layer and both are displayed while spacing apart both layers.

FIG. 5 shows the up and down relationship of the two dimensional brain wave measurement image and living body optical measurement image in an inverted manner as that shown in FIG. 2 and displays both images in a spaced apart manner, in which in order to easily discriminate measurement positions while displaying the two kinds of two dimensional images simultaneously, the two dimensional images of two layers are displayed on two planes of different heights in a three dimensional space. The up and down relationship of both display layers above can be inverted, further, the up and down relationship can be designed to be able to arbitrarily designate depending on desire of the observer via the console 260.

FIG. 6 shows time course maps displaying time course graphs of the brain wave measurement and living body optical measurement at respective measurement positions and the corresponding graphs are displayed in parallel on the two kinds of respective time course maps, thereby, a relationship of both signals at the respective measurement points can be easily observed.

In the above display, the two kinds of data are displayed in parallel and the mutual relationship between the signals is judged by the observer, however, when the relationship between the two signals is processed mathematically and the result is displayed, a load of the observer can be further reduced.

FIG. 7 is an example in which values of two data at respective points of two images representing spatial distribution of two kinds of signals, in that a spatial distribution (a) of the optical measurement signals and a spatial distribution (b) of the brain wave measurement signals, are multiplied, and the result is newly constituted as a composite image (c) and displayed. As a result, since at the portion where the signals of both data increase at the same time the composite image is emphasized, thereby, the relationship between two signals is clearly presented.

Herein for the computation of the two signals a function optimized theoretically or experimentally can be used depending on the objective phenomenon to be observed. For example, as shown in FIG. 8, both data with regard to intensities of brain wave measurement signals (a) and living body optical measurement signals (b) at a certain measurement point are normalized with the maximum values and through plotting these two data on a perpendicularly crossing axes using time as a parameter, a diagram (c) representing a correlation of both data at the certain measurement point is constituted, with this diagram, for example, correlation coefficients, phase differences at respective measurement points and area of the diagram are determined and these can be displayed in two dimensional images.

Figure 9:
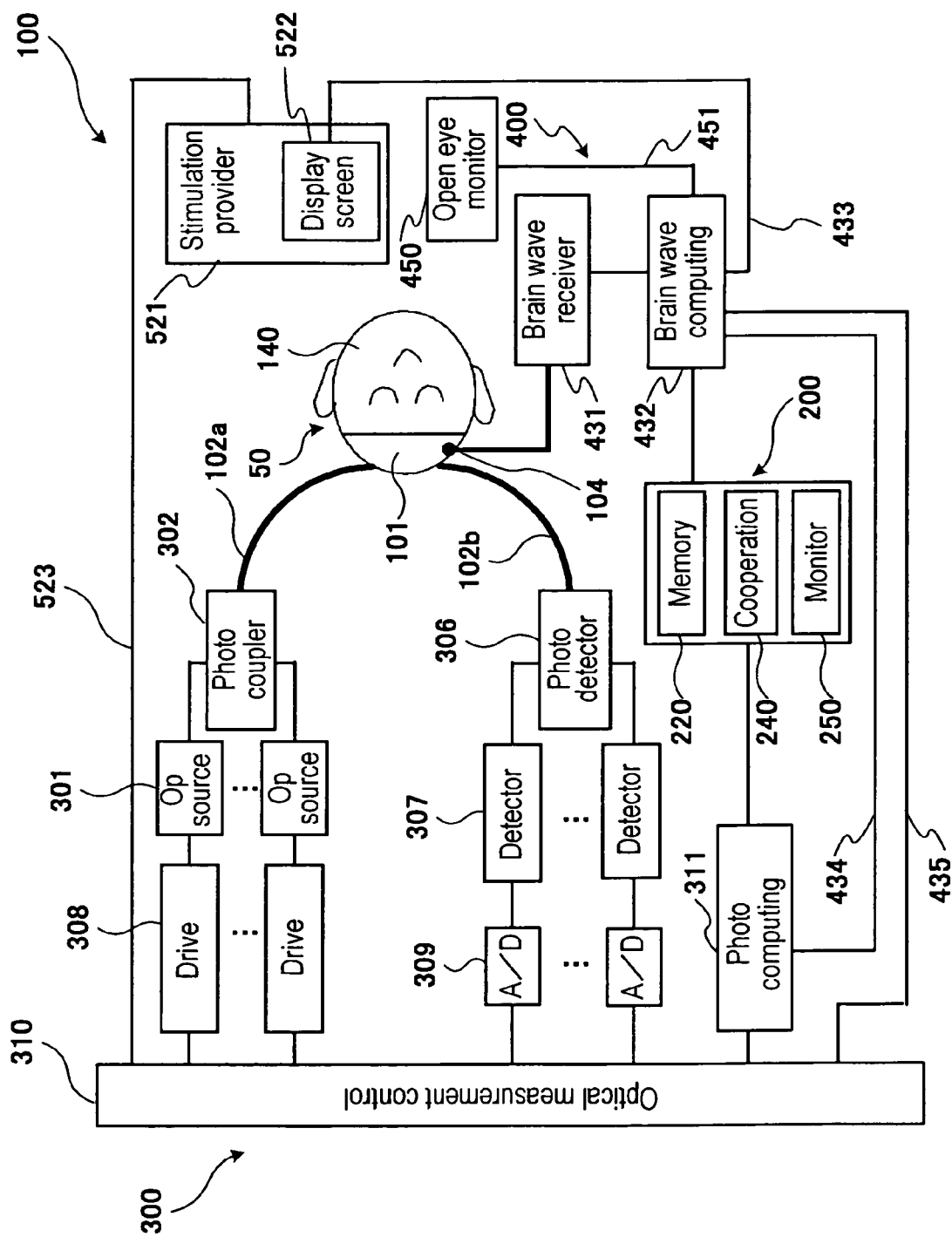
FIG. 9 is a block diagram showing schematically a living body information signal processing system with a device for providing stimulation to a subject according to another embodiment of the present invention.

FIG. 9 shows an entire constitutional diagram of another embodiment of the living body information signal processing system according to the present invention. The present embodiment is a system, which combines an optical measurement apparatus and a brain wave measurement apparatus. In the drawing, a plurality of optical sources (in the illustrated example, two sources) 301 generate near infrared light having wavelengths of about 600~1200 nm which easily penetrates human body. The near infrared light generated from the optical sources 301 is led to an optical directional coupler (photo-coupler) 302 via an optical fiber and mixed there, and coupled in an irradiation use optical fiber 102a in a transmittable manner. A top end of the optical fiber 102a is attached to a head cap 101 in a manner to be held at a desired position on a head portion of a subject 140.

On the head cap 101 a top end of a light collecting use optical fiber 102b is secured which leads penetration light signal retuned to the outside from the inside of head of the subject while scattering therein to a photo detector 306. The photo detector 306 is constituted by such as a photodiode and a photo multiplier tube and converts input optical signals into electrical signals. The optical signals converted into electrical signals by the photo detector 306 are input to a plurality (in the illustrated example, two sources) of phase detectors (wave detectors (in the illustrated example, two detectors)) 307. The phase detector 307 performs filtering with reference to a modulation frequency set for every optical sources 301 and outputs an optical amount of the corresponding optical signal for every optical sources 301 to an A/D converter 309. The A/D converter 309 converts the detected optical amount of the optical signal to digital data and output the same to an optical measurement control device 310.

The optical measurement control device 310 controls such as the optical intensity of the respective optical sources 301 such as laser diodes and the amplification of the photo detector 306 via a driving device 308 for the optical sources 301 as well as controls the living body optical measurement from the beginning to the end. An optical computing device 311 calculates variation amount of oxy-hemoglobin, deoxy-hemoglobin and total hemoglobin in the subject 140 from two or three kinds of near infrared light pairs passed a same portion in the subject 140 by making use of the detected optical amount of the respective optical sources output from the A/D converter 309. Optical measurement data representing the calculation result are displayed on a monitor 250 serving as a display device in numerical values or in image forms as well as stored in a memory 220. Further, a stimulation providing device 521 is a device, which is disposed, for example, near the head portion of the subject 140 and provides stimulation such as sound and image to the subject 140.

On the other hand, the brain wave measurement apparatus 400 is constituted by including brain wave electrodes 104 disposed on the head portion of the subject 140, a brain wave receiving device 431 and a brain wave computing device 432. The brain wave receiving device 431 receives a variation of the brain wave detected by the brain wave electrodes 104 and displays the same on the monitor 250 as well as outputs the same to the brain wave computing device 432. The brain wave computing device 432 detects brain waves such as $\theta$ wave and $\beta$ wave based on the input brain waves and determines conditions such as physical condition (for example, sleepiness) of the subject 140 based on the detection. Computing results such as magnitudes and ratio of the $\theta$ wave and $\beta$ wave detected by the brain wave computing device 432 are output on a display screen 522 provided for the stimulation providing device 521. When the magnitudes and ratio of such as the $\theta$ wave and $\beta$ wave inputted exceed over or fall below a set value, the stimulation providing device 521 is constituted so as to output a trigger signal 523 to the optical measurement control device 310 and to perform controls of termination, pause and start of the optical measurement.

Namely in the optical measurement, it is desired to measure a relationship between timing when stimulation to ear or eye of the subject 140 is given by the stimulation providing device 521 and a variation of the brain function, for example, a variation of the brain function before and after providing the stimulation. Therefore, in the present embodiment, the optical measurement control device 310 performs controls of termination, pause and start of the optical measurement depending on the brain condition of the subject, for example, whether the brain is awakened with the trigger signal 523 output from the stimulation providing device 521.

The operation and manner of use of the thus constituted present embodiment will be explained in detail herein below. When performing the optical measurement of the active condition of the brain, it is at first necessary to hold the measurement condition at a constant level such as controlling the active condition of the brain of the subject 140 at a constant or a desired condition. Herein below, the operation and manner of use of the present embodiment will be explained according to classified measurement modes depending on the optical measurement purposes. Further, the measurement modes explained below can be activated or used independently each other or in proper combinations of the plurality of the modes.

(Optical Measurement Control Mode with Attention Drawing Function to Subject)

Figure 10:
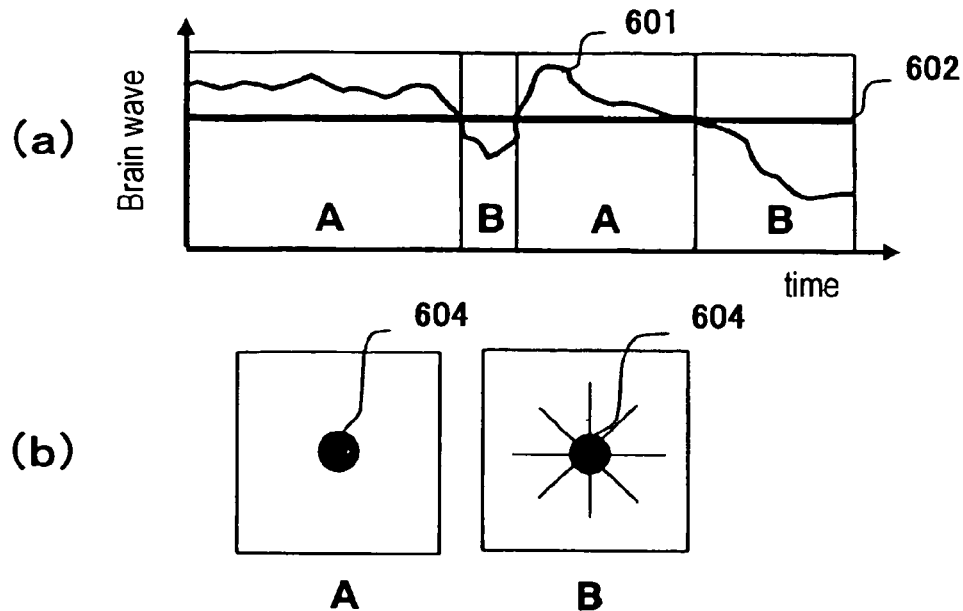
FIG. 10 is a diagram for explaining of providing stimulation for drawing attention of a subject by making use of levels of brain wave in the embodiment as shown in FIG. 9.

In a case when performing the optical measurement of the active condition of the brain, as an example of measuring the active condition of the brain of the subject 140 while maintaining the same at a constant condition, it is necessary to draw attention of the subject 140, for example, so as not to sleep. In this instance, as shown in FIG. 10, an image for drawing attention is displayed on the display screen 522 of the stimulation providing device 521. A curve 601 in (a) of the drawing shows time variation of awakening degree of the subject computed by the brain wave computing device 432. A line 602 in (a) of the drawing shows a judgment threshold value with regard to awakening degree for drawing attention. When the awakening degree falls below the judgment threshold value as shown in period B in the drawing, a lamp 604 for drawing attention is lighted as shown by B in (b) of the drawing and when the awakening degree exceeds over the judgment threshold value as shown in period A in the drawing, the lamp 604 is unlighted as shown by A in (b) of the drawing. Thereby, the optical measurement condition is kept in a constant allowable range.

Figure 11:
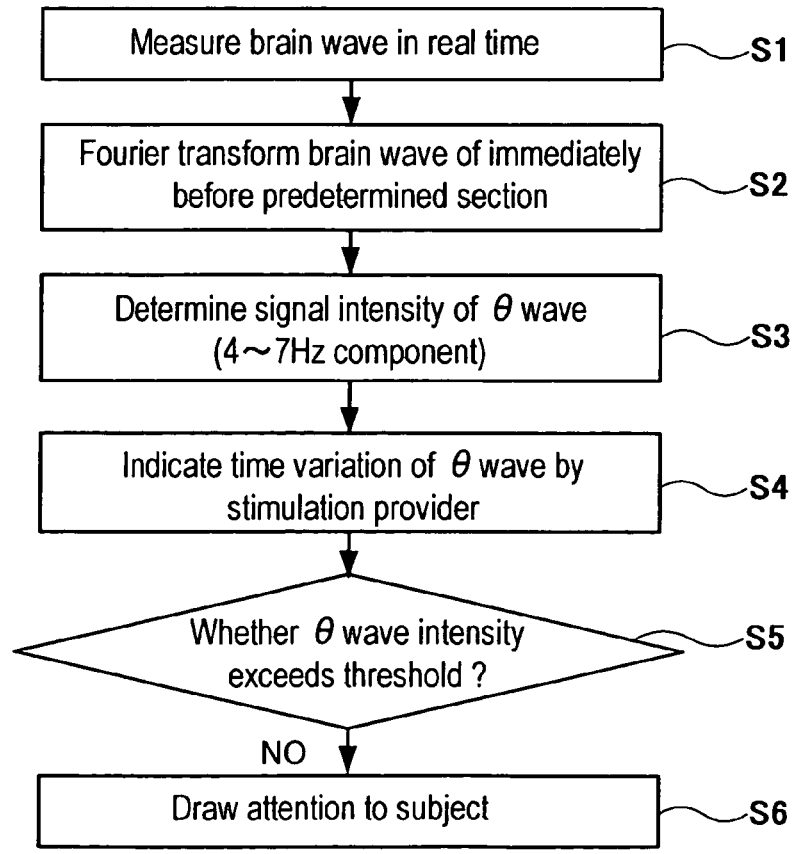
FIG. 11 is a flowchart for explaining processing sequence of providing stimulation for drawing attention of a subject by making use of levels of brain wave in the embodiment as shown in FIG. 9.

FIG. 11 shows an example of a sequence in which the degree of awakening is computed by the brain wave computing device 432, the degree of awakening is judged and stimulation for drawing attention is given. As shown in FIG. 11, the brain wave computing device 432 measures in real time the brain waves input from the brain wave receiving device 431 (S1), and the brain wave data of a predetermined section (sampling cycle) of immediately before are Fourier transformed for every sampling cycle (S2). Subsequently, signal intensity of $\theta$ wave (4~7 Hz components) in the brain waves indicating moving to sleep, in that dozing of the subject is determined (S3). The determined signal intensity of θ wave is displayed on the display screen 522 of the stimulation providing device 521 as the degree of awakening depending on necessity. Subsequently, it is judged whether the signal intensity of θ wave exceeds over a judgment threshold value set in advance (S5). When not exceeding, in order to draw attention of the subject a display of attention drawing is given on the display screen 522 (S6). When the signal intensity of θ wave exceeds over a judgment threshold value, no display of attention drawing is given on the display screen 522.

Herein, as possible causes which require the attention drawing of the subject, other than the degree of awakening there include an attention intensity which can be measured from the brain waves and a body motion which can be measured from myoelectric signals which will be explained later. Further, as the methods of drawing attention, when measuring a brain reaction to sound, it is preferable to display an image on the display screen 522, and when measuring a brain reaction to vision, it is preferable to use sound. Further, the attention drawing can be achieved, for example, by variation of alarm sound, variation of frequency, variation of touch sense temperature) or influencing to eyesight such as with an image for drawing attention and graphs of the computing result.

In this way, by displaying the computation result of the brain waves on the display screen 522 of the stimulation providing device 521 and by feeding back such as sleepiness and reduction of the attention intensity to the subject 140, the brain function measurement by the optical measurement can be performed under a condition in which a desired brain activeness is kept, for example, under "awakened condition". As a result, a loss of obtained optical measurement data can be reduced and the computing load for the optical measurement can be lightened.

Although, in FIGS. 10 and 11 examples, use of θ wave in the brain waves is explained, the entirely the same attention drawing can be achieved by making use of β wave (14~33 Hz). Namely, the β wave represents a condition when the subject is under high tension, high attentiveness or high cognition, and when the subject is performing a matter which requires attentiveness, the β wave appears. Further, when the subject is concentrating on such as a movie and TV, α wave appears, however, since the α wave relates to a passive attentiveness, which is different from the attention used for the brain function measurement. On the other hand, since the attentiveness of the β wave is a positive one, it is preferable to use the variation of the β wave for the evaluation of the attention.

(Optical Measurement Control Mode 1 According to Brain Condition)

In the optical measurement, generally, noises included in the measurement data are reduced in such a manner that the optical measurement data are collected over a plurality of sampling cycles and the collected data are added. For this reason, the measurement time under the same measurement condition is prolonged and if the condition of the brain changes during that time, it is possible that the collected data become ineffective. Therefore, in the present embodiment, brain wave data 434 are sent from the brain wave computing device 432 to an optical computing device 311 and in the optical computing device 311 the optical data sampled are adopted or rejected depending on the active condition of the brain.

Figure 12:
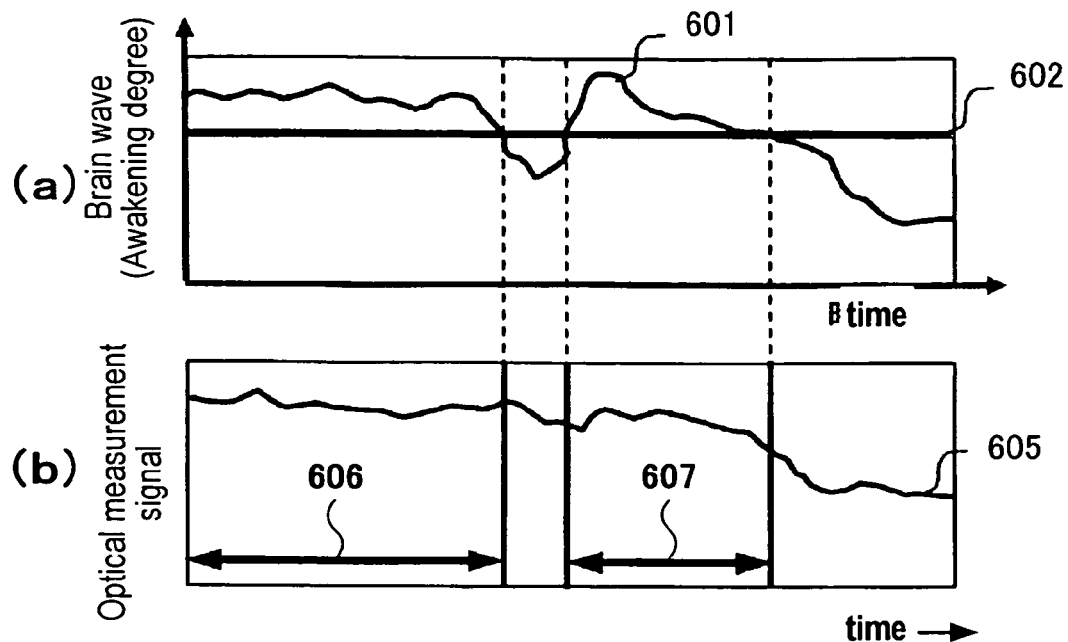
FIG. 12 is a diagram for explaining adoption or rejection of optical measurement data by making use of levels of brain wave in the embodiment as shown in FIG. 9.
Figure 13:
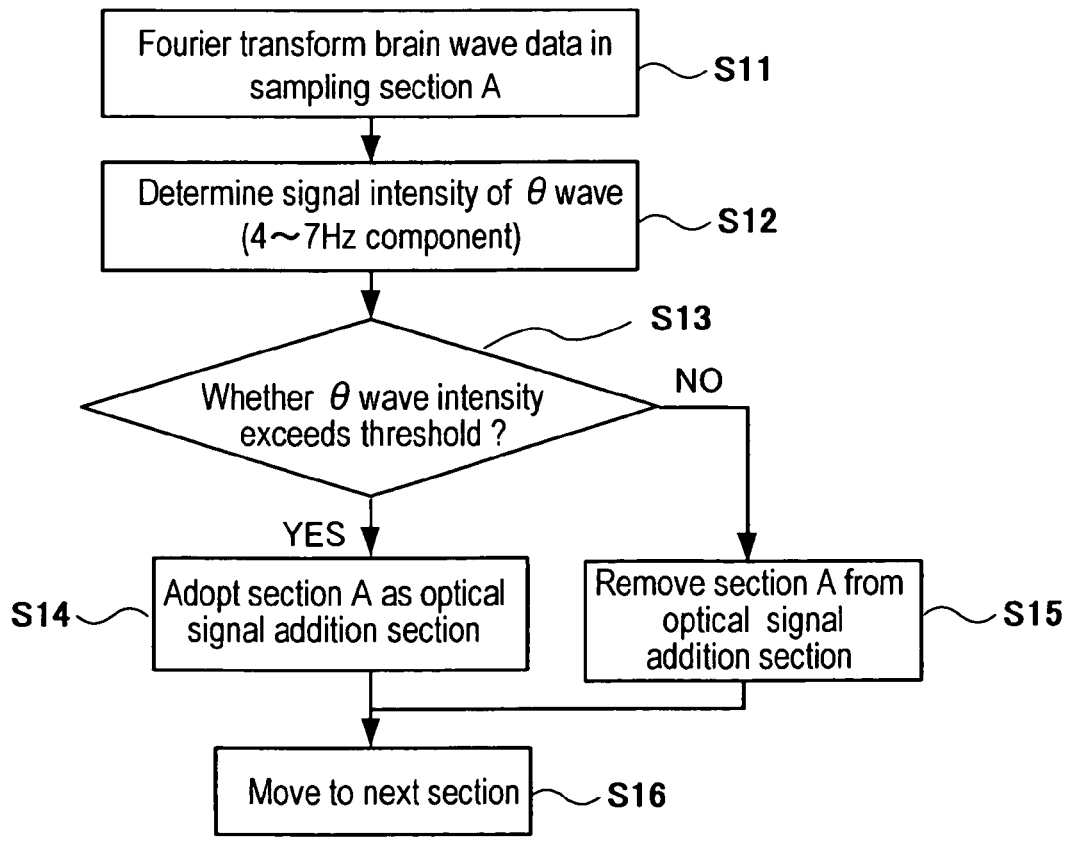
FIG. 13 is a flowchart for explaining a processing sequence of adoption or rejection of optical measurement data by making use of levels of brain wave in the embodiment as shown in FIG. 9.

FIG. 12 (*a*) is the same diagram as FIG. 10 (*a*), a curve 601 shows time variation of awakening degree (attention intensity) of the subject computed by the brain wave computing device 432. A line 602 in (a) of the drawing shows a judgment threshold value with regard to awakening degree (attention intensity) for drawing attention. Further, a curve 605 in (b) of the drawing represents a time variation of the optical measurement data computed by the optical computing device 311 for the corresponding time. With the brain wave computing device 432 or the optical computing device 311, the attention intensity is judged according to the processing sequence as shown in FIG. 13 and the adoption or rejection of the optical measurement data is performed. At first, brain wave data in an arbitrary measurement section A are Fourier transformed (S11). Subsequently, signal intensity of θ wave (4~7 Hz components) in the brain waves indicating moving to sleep, in that dozing of the subject is determined (S12). It is judged whether the determined signal intensity of θ wave exceeds over a judgment threshold value set in advance (S13). When the signal intensity of θ wave exceeds over a judgment threshold value, the section A is adopted as the addition section of the optical measurement data (S14) and when not exceeding, the section A is removed from the addition section of the optical measurement data (S15) and moves to the following section (S16). Namely, a processing is performed in which the optical measurement data sampled in sections 606 and 607 in FIG. 12 (*b*) where the attention intensity exceeds over the judgment threshold value 602 are added and the optical measurement data of the other sections are rejected for adding.

In this instance, when storing the optical measurement data in the memory 220, the data is stored while adding markers indicating the start point and ending point of the adding sections 606 and 607. Further, the falling down of the θ wave signal intensity below the threshold value represents a condition of moving into sleep, in that dozing, if not awaken, the subject will possibly move into deep sleep, there will be a case to add evaluation of δ wave (1.5~4 Hz).

According to the optical measurement control mode 1, the optical data outside the measurement condition can be discarded, an accuracy of the optical measurement can be enhanced. Further, the measurement times to be repeated for enhancing the measurement accuracy are reduced, thereby, the substantial measurement time is shortened.

Figure 14:
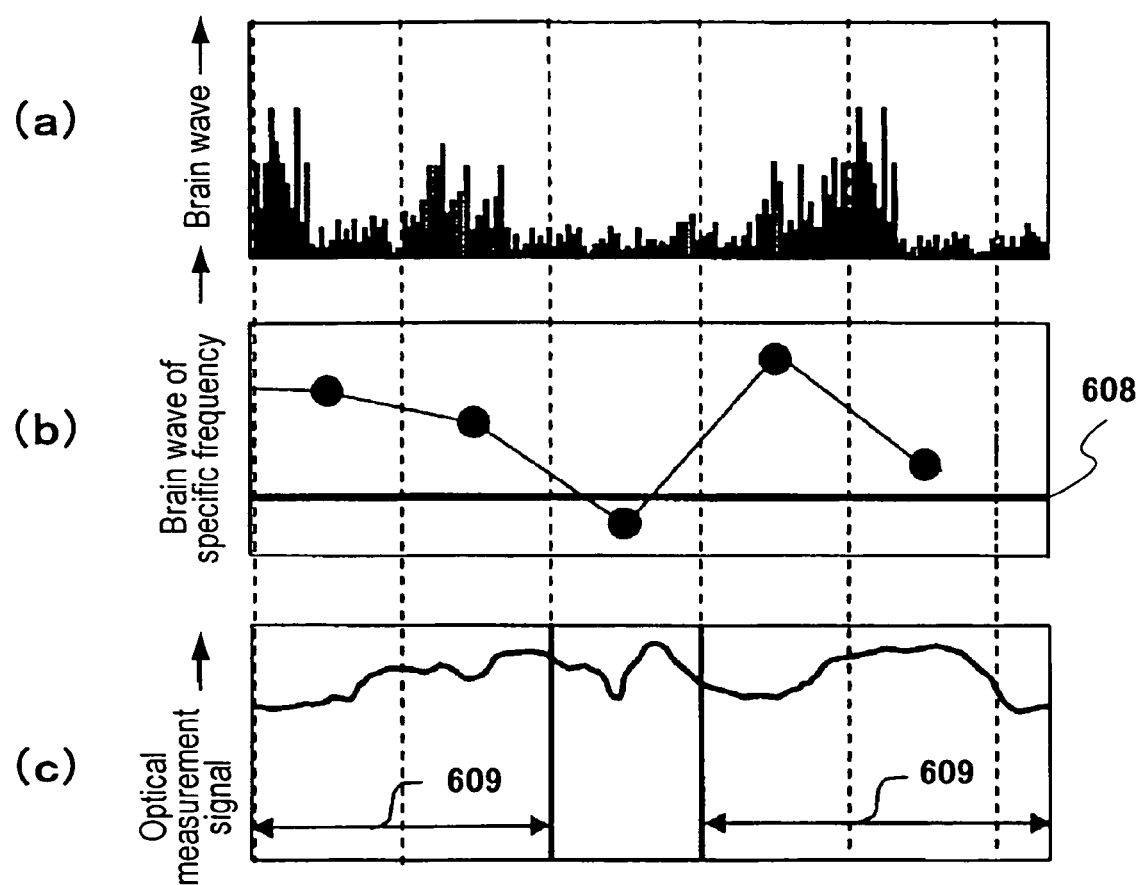
FIG. 14 is a diagram for explaining adoption or rejection of optical measurement data by making use of levels of a specific frequency in brain waves in the embodiment as shown in FIG. 9.

Further, like the alternative as explained in connection with FIG. 11 example, in FIG. 13 example, in place of the θ wave, the adoption or rejection of the measurement data can be performed through judgment of the attention intensity based on the β wave. FIG. 14 exemplarily shows waveform diagrams when performing the adoption or rejection of the measurement data based on the brain waves of other specific frequencies. (a) in the drawing shows a waveform diagram of the brain waves, (b) in the drawing shows an example of waveform in the specific frequency band included in the brain waves and (c) in the drawing shows an example of optical measurement data waveform along the same time axis. As seen from the drawing, when the brain wave in the specific frequency band falls below a judgment threshold value 608, the optical measurement data are discarded and the optical measurement data in the other sections 609 and 609 are added.

(Optical Measurement Control Mode 2 According to Brain Condition)

Among brain diseases there are diseases, for example, such as epilepsy of which appearance is uncertain. With regard to an attack of these brain diseases, although it is important to observe the brain condition before and after the attack, however, since it is uncertain when the disease appears, it is necessary to perform the optical measurement for a long time which causes a problem that the burden of the subject for the measurement is significant. Further, since it is necessary to store great many optical measurement data for a long time, a memory having a large memory capacity is required.

Therefore, when an attack of epilepsy is detected according to the diagnosis result by the brain wave computing device 432, the trigger signal 435 as shown in FIG. 9 is sent to the optical measurement control device 310. When the optical measurement control device 310 receives the trigger signal 435, only the optical measurement data of a predetermined period before the signal reception are stored in the memory 220. Thereby, the memory capacity of the memory 220 can be saved. Further, the brain wave computing device 432 sends the detection of epilepsy attack to the stimulation providing device 521 and causes to display the same on the display screen 522.

As has been explained above, according to FIG. 9 embodiment, when variation amount of oxy hemoglobin, deoxy hemoglobin and total hemoglobin in the intra brain of the subject 140 before and after such as audible and visible stimulation is given to the subject 140 and, for example, images the same, a brain function measurement can be performed through observation of the variation of the brain condition.

In particular, according to the present embodiment, the brain function measurement by the optical measurement can be performed under a condition in which a desired brain activeness is kept, for example under "awakened condition". As a result, a loss of obtained optical measurement data can be reduced and the computing load for the optical measurement can be lightened.

Further, since the optical measurement result is computed after selecting the optical measurement data, which meet the measurement condition, the accuracy of the optical measurement can be enhanced.

Further, although not illustrated, as an alternative of the present embodiment, in place of the brain wave measurement device a body motion detecting device can be used.

The body motion detecting device is constituted by including myoelectric electrodes attached in contact to such as a neck of the subject 140, a myoelectric receiving device which receives myoelectric signals detected by the myoelectric electrodes and a body motion computing device which computes a body motion based on the myoelectric signals received by the myoelectric receiving device. The body motion computing device, for example, detects that the subject 140 moved the head portion and, for example, displays the same on the display screen 522 of the stimulation providing device 521 to feed back the same to the subject 140.

According to the present variation, like the awakening degree in the brain waves (attention intensity), through comparison with a judgment threshold value (corresponding to 602 in FIG. 10) corresponding to an allowable value set in advance of the body motion amount, the operation or the manner of use corresponding to the attention drawing mode for the subject and to the optical measurement control modes 1 and 2 can be realized. Further, oppositely, an optical measurement of the brain condition when the subject moved can also be performed.

Figure 15:
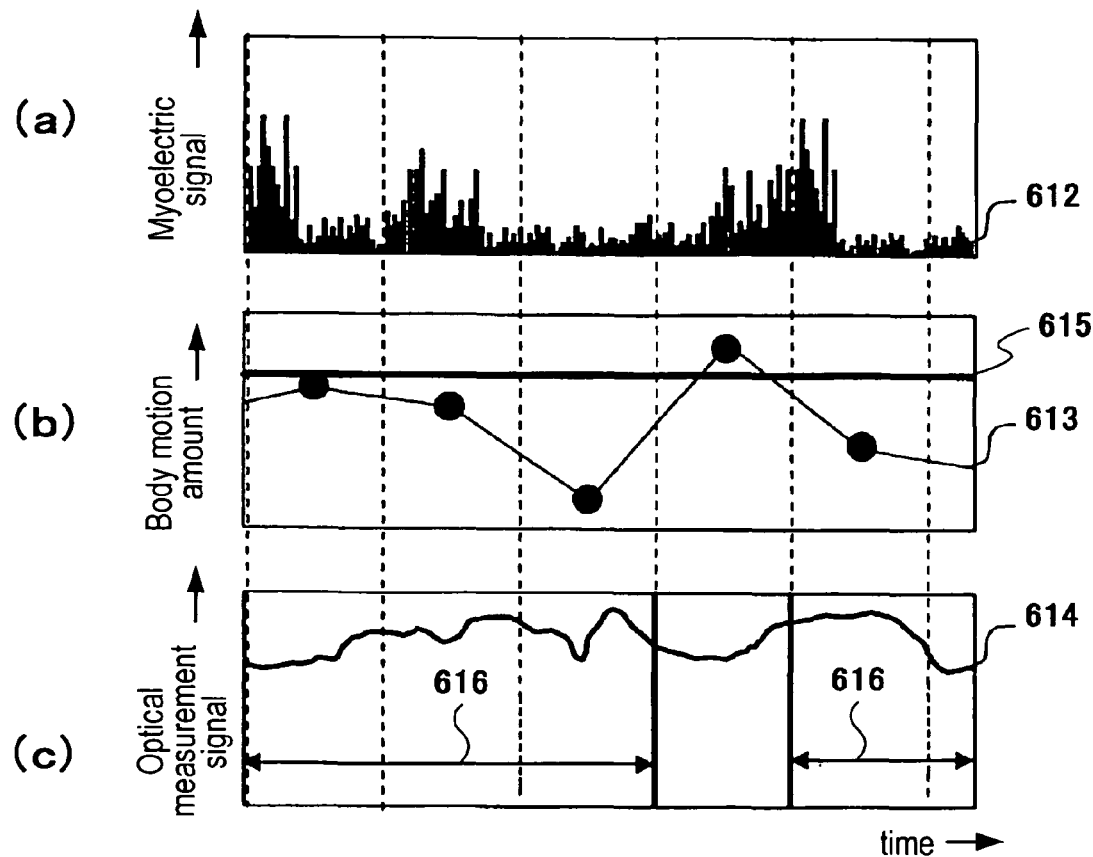
FIG. 15 is a diagram for explaining adoption or rejection of optical measurement data by making use of levels of body motion amount in an alternative example in which a body motion detection device is used in place of the brain wave measurement device in the embodiment as shown in FIG. 9.

Namely, in the case of the optical measurement control mode with the attention drawing for the subject which uses the body motion amount as a parameter, like the processing sequence as shown in FIG. 11, the myoelectric signals are measured in real time, the body motion amount is determined from the myoelectric data in a sample period immediately before, whether the body motion amount exceeds over the judgment threshold value is judged and when exceeding, an attention drawing such as "don't move" is given, for example, on the display screen 522. Respective waveforms at this moment of myoelectric signal 612, body motion amount 613 and optical measurement data 613 are shown in FIGS. 15(a)~(c). As shown in the drawing, whether the body motion amount 613 which is obtained by integrating the myoelectric signals 612 exceeds over the judgment threshold value 615 is judged, and the optical measurement data of the section exceeding are discarded and the optical measurement data of the sections not exceeding 616 and 616 are added.

Further, like the processing sequence as shown in FIG. 13, the following process is performed for every section, in that a body motion amount is determined from the myoelectric data of section A, whether the body motion amount exceeds over the judgment threshold value is judged, and when exceeding, the optical measurement data of the section A are removed from the addition section and when not exceeding over the judgment threshold value, the section A is selected as an addition section. Thereby, since the optical measurement result is computed after selecting the optical measurement data, which meet the measurement condition, the accuracy of the optical measurement can be enhanced.

(Inherent Example of Optical Measurement Control Mode with Body Motion Amount)

Figure 16:
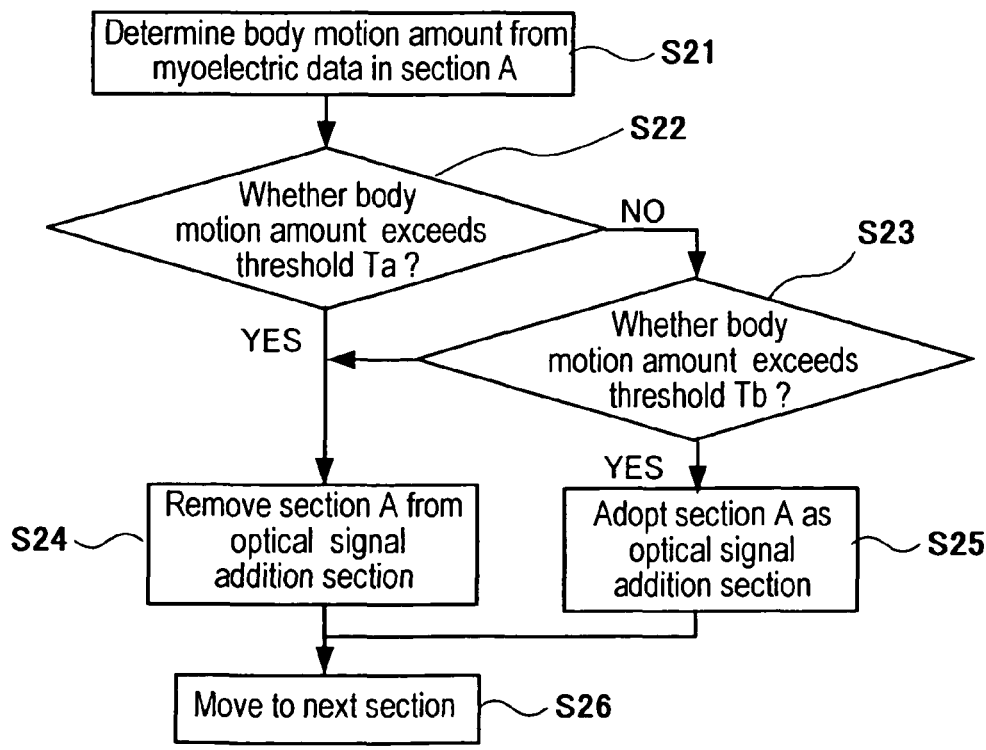
FIG. 16 is a flowchart for explaining a processing sequence of adoption or rejection of optical measurement data by making use of levels of body motion amount in the alternative of FIG. 9 embodiment as shown in FIG. 15.

FIG. 16 shows a processing example of measurement mode inherent to body motion. In a case of babies, a baby sometimes not starts task (such as a motion) in response to a signal from an inspector. In such instance, a motion such as mouth and hand is detected from myoelectric signals and a period in which the motion is above a predetermined threshold value is treated as a task period. However, measurement data in a section in which the body motion is extremely large and the brain function measurement through the optical measurement is difficult can be removed. Namely, as shown in FIG. 16, a body motion amount is determined from the myoelectric data of the section A (S21). Subsequently, whether the determined body motion amount exceeds over a first judgment threshold value Ta is judged (S22). When exceeding, the optical measurement data of the section A are removed from the addition section (S24). On one hand, when the body motion amount does not exceed the judgment threshold value Ta, whether the body motion amount exceeds over a second judgment threshold value Tb (wherein, Ta>Tb) is judged (S23). When the body motion exceeds over Tb, namely, when Tb<body motion amount<Ta, the optical measurement data of the section A is selected for the addition section (S25). On the other hand, when the body motion amount falls below Tb, the process moves to step S24 and the optical measurement data of the section A are removed from the addition section. After completing these processing, the process moves to the following section (S26).

Further, in place of the step S21, a body motion amount is determined by measuring myoelectric data in real time, in place of the steps S24 and S25, when Tb<body motion amount<Ta, an image a baby likes is displayed on the display screen 522 of the stimulation providing device 521, and when body motion amount<Ta, or body motion amount<Tb, an image a baby dislikes can be displayed on the display screen 522. Namely, in order to maintain the body motion at the current state, an image a baby likes is displayed. When suppression of body motion is desired, an animation of slow tempo is displayed and when a body motion increase is desired, an animation of up-tempo including an image a baby comparatively dislikes is displayed.

Now an open eye monitor 50 in FIG. 9 embodiment will be explained.

Since the amount of α wave in the brain waves decreases in response to eye opening, in order to enhance the measurement accuracy with the α wave, it is necessary to change the evaluation of the measured a wave depending on when the eye is opened and when closed. In particular, such is necessary when measuring the brain function of a baby. For this reason, in the present embodiment, the open eye monitor 450, which detects open and close condition of eye is provided and a detection signal 451 of the open eye monitor 450 is designed to be input to the brain wave computing device 432.

The open eye monitor 450 takes an image of an eyeball in real time such as by a CCD camera and detects an opening degree using the area of iris of the eye as an evaluation function. Namely, as shown in FIG. 17, the open eye states are classified into a plurality of levels such as closed state, half opened state and fully opened state and a calibration curve 620 relating to the intensity of α wave at respective states is set in advance based on a plurality of measured data.

With the calibration curve, according to the present embodiment, since a calibration of the α wave can be performed in the brain wave computing device 432 according to the open eye state, the measurement accuracy of the α wave can be enhanced. As a result, proper contents of stimulation can be given from the stimulation providing device 521.

In the living body information signal processing system according to the present invention as has been explained above, since the physical amounts of the measurement object and the measurement principles of the optical measurement and the brain wave measurement are different, it is preferable to cooperate the measurement control. Namely, although both optical measurement and brain wave measurement measure variations of brain function in response to stimulations, in order to enhance the accuracy of the measured values, in both measurements, sampling data of a plurality of times with respect to the same stimulation are added.

Figures 17, 18:
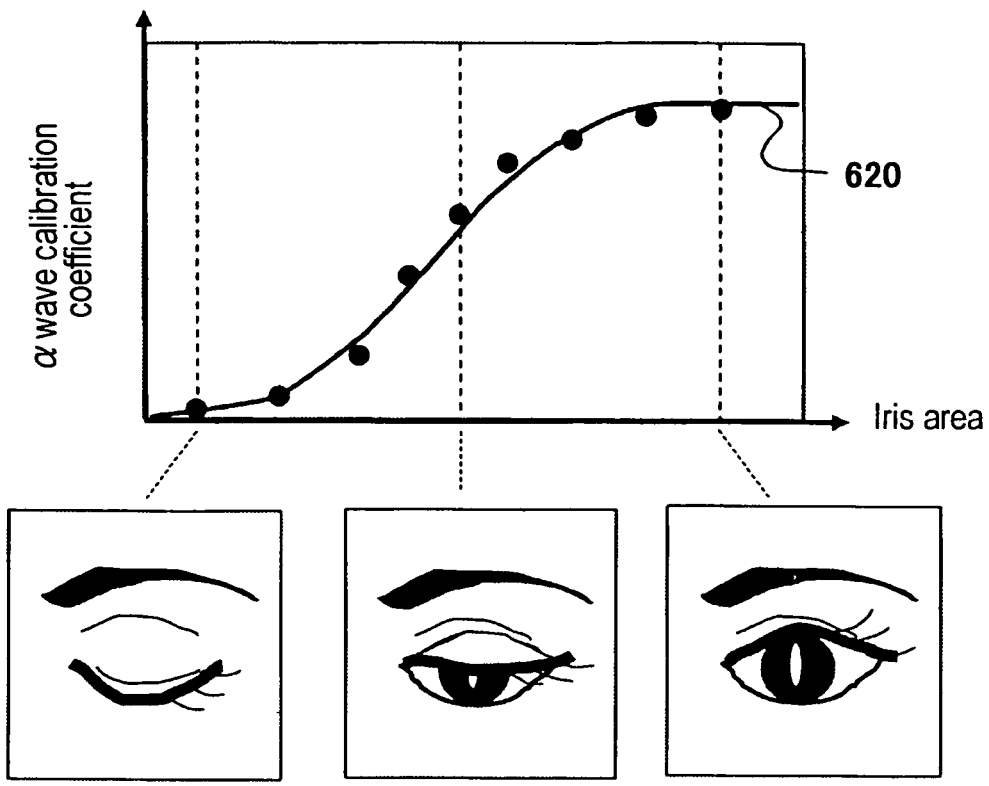
FIG. 17 is a diagram for explaining a relationship between degree of open eye and α wave in brain waves in connection with an open eye monitor used in the embodiment as shown in FIG. 9.
FIG. 18 is a diagram for explaining differences between optical measurement and brain wave measurement.

However, because of the difference of the measurement principle, as shown in FIG. 18, when a typical event related potentials (ERP) for the brain wave measurement is used, an interval (stimulation interval) for giving a stimulation is, for example, 0.1~1 s and necessary number of additions is 20~200 times, on the other hand, in case of the optical measurement, the stimulation interval is 15~30 s and the necessary number of additions is 5~10 times. Namely, the necessity of the cooperative control is caused by the following facts that in the case of the brain waves, the reaction can be detected in a few 10 ms after giving stimulation, on the other hand, in the case of the optical measurement in which a variation of concentration of hemoglobin in blood is measured, it takes more than 10~15 s until the blood state varies after stimulation is given.

Figure 19:
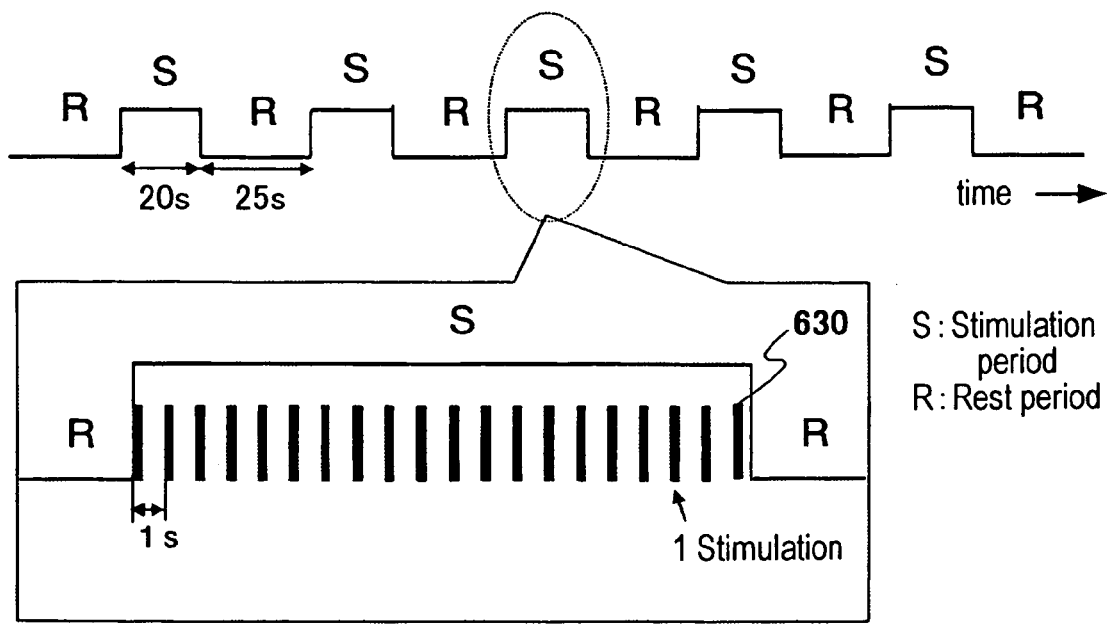
FIG. 19 is a diagram showing an example of timing pattern of providing stimulation for optical measurement and brain wave measurement in the embodiment as shown in FIG. 9.
Figure 20:
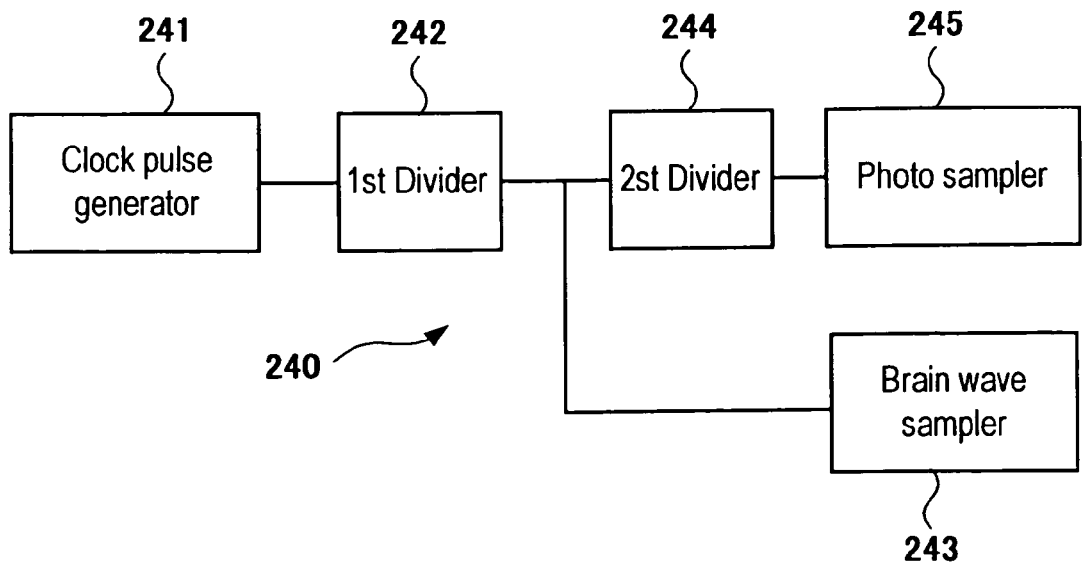
FIG. 20 is a block diagram of an example of a sampling pulse producing circuit for optical measurement and brain wave measurement in a cooperative control unit in the embodiment as shown in FIG. 9.
Figure 21:
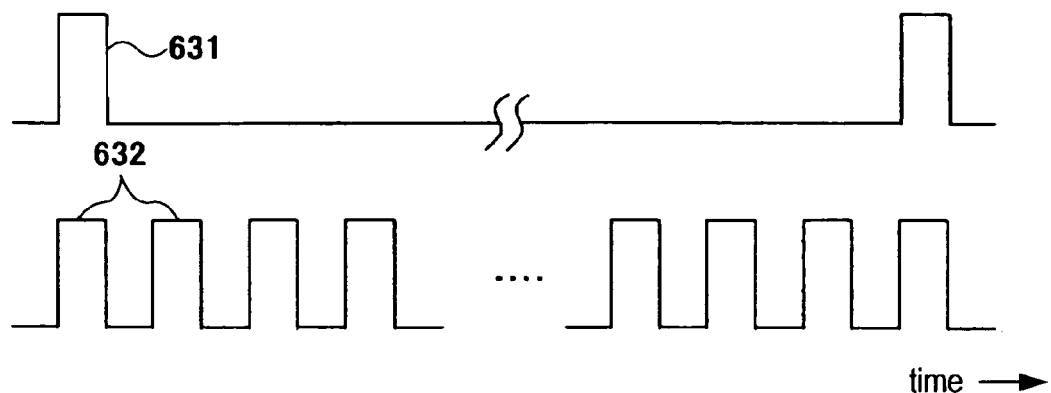
FIG. 21 is a time chart of sampling pulses produced by the sampling pulse producing circuit as shown in FIG. 20.

For this reason, in the present embodiment, as shown in FIG. 19, when a measurement is performed by repeating alternatively stimulation periods S and rest periods R, while repeating a unit stimulation 630 having a stimulation period of 1 s, data for the brain wave measurement can be added 100 times and data for the optical measurement having a unit stimulation providing interval of 20 s can be added 5 times. As a result, the optical measurement and the brain wave measurement can be cooperated. The cooperative measurement can be realized by a sampling pulse producing means constituting the cooperative control unit 240 as shown in FIG. 20. Namely, as shown in the drawing, clock pulses generated from a clock pulse generator 241 are divided into clock pulses suitable for the brain wave measurement by a first divider 242 to provide stimulations as well as are supplied to a brain wave measurement use sampling unit 243. Further, the clock pulses divided by the first divider 242 are further divided by a second divider 244 to provide stimulations as well as are supplied to an optical measurement use sampling unit 245. With this measure, from the sampling units 245 and 243, sampling pulses 631 and 632 are respectively output and the optical data and the brain wave data are sampled at a set timing.

Figure 22:
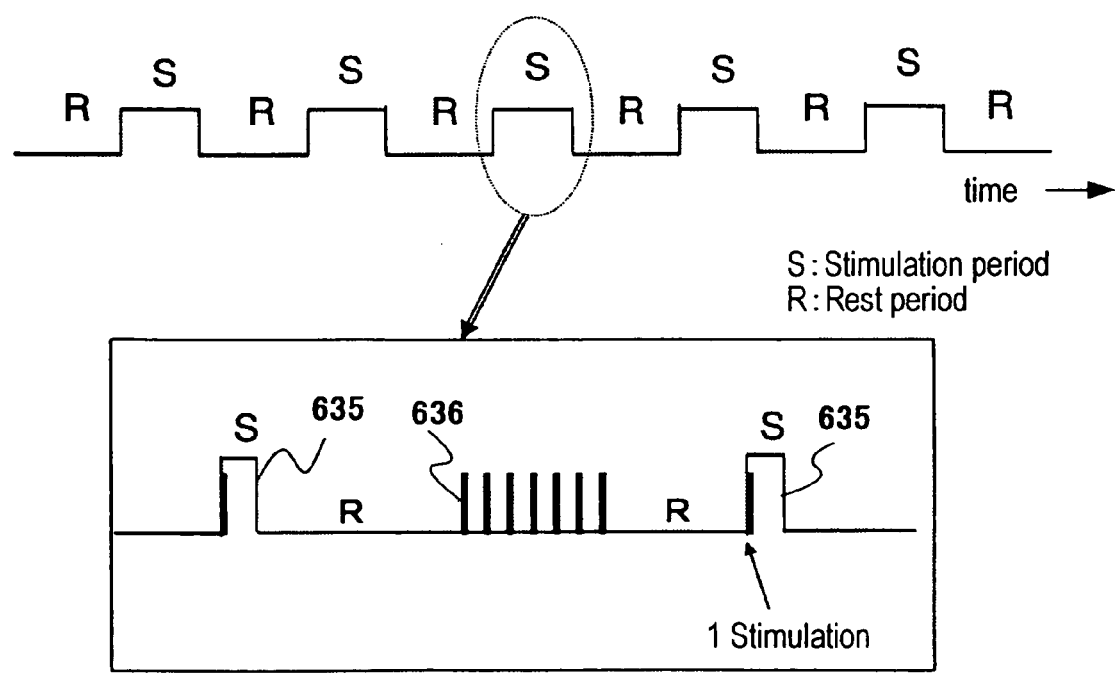
FIG. 22 is a diagram showing another example of timing pattern of providing stimulation for optical measurement and brain wave measurement in the embodiment as shown in FIG. 9.

FIG. 22 shows another embodiment for the measurement cooperative control. In the present embodiment, same stimulation is used for the optical measurement and the brain wave measurement, and for every optical measurement and brain wave measurement the stimulation is added once. The stimulation time of the optical measurement 635 is minimized and a reaction with respect to the stimulation in one time is measured. The stimulation for the brain wave measurement 636 is added between the optical measurements 635 and 635, and the measurement times are increased. A necessary rest time should be placed before and after the stimulation for the optical measurement.

As has been explained above, through effecting the measurement cooperation for the optical measurement and the brain wave measurement, correspondence of the brain function measurement by the optical measurement and the brain wave measurement can be achieved in short time without damaging the measurement characteristics of both.

Figure 23:
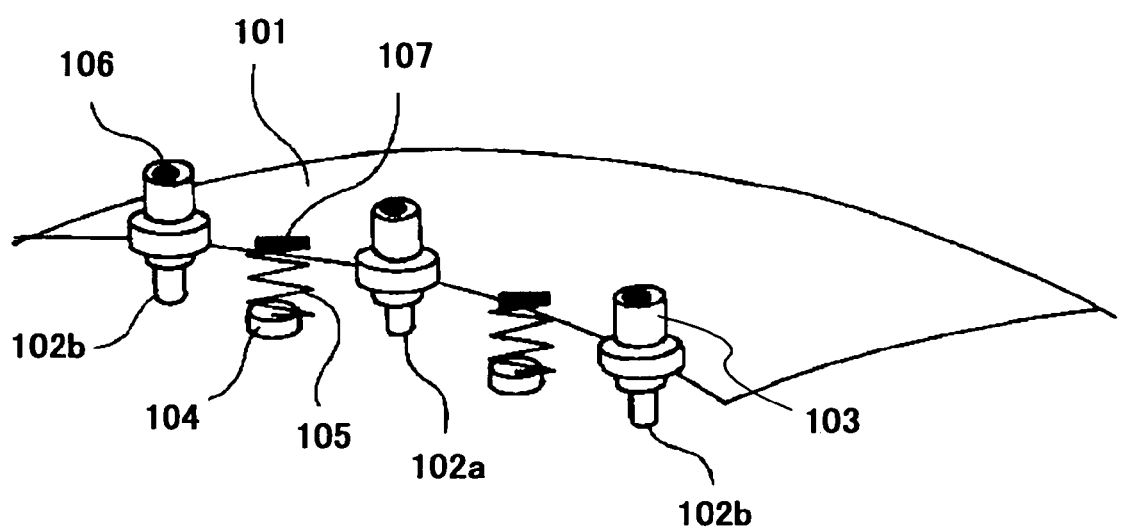
FIG. 23 is a partially cross sectioned perspective view representing a first embodiment of a probe device used in a living body signal processing system according to the present invention.

FIG. 23 is a partially cross sectioned perspective view showing one embodiment of a probe device 50 used for the living body signal processing system according to the present invention. In FIG. 23, a part of a holder 101 made of rubber, plastic or cloth is shown being cut. In the drawing, the holder 101 is mounted on the head portion of the subject (living body). On the holder 101, a plurality of irradiation use optical fibers 102a for irradiating inspection light of such as near infrared light onto the head portion and a plurality of light receiving use optical fibers 102b for receiving penetration light of the inspection light are disposed with a predetermined interval each other. The respective irradiation use optical fibers 102a are disposed at an intermediate between the mutually adjacent light receiving use optical fibers 102b. In FIG. 23, although only one irradiation use optical fiber 102a and two light receiving use optical fibers 102b are shown, actually, the plurality of irradiation use optical fibers 102a and the plurality of light receiving use optical fibers 102b are disposed in a lattice pattern.

The respective optical fibers 102a and 102b are attached to the holder 101 by means of optical fiber attachments 103. In each of the optical fiber attachments 103, a spring for the fiber (not shown) is built-in. The spring for the fiber is compressed when the optical fibers 102a and 102b are pressed onto the head portion of the subject. In this instance, because of the restoring force of the spring for the fiber the top end portions of the optical fibers 102a and 102b are pressed onto the head portion of the subject.

On the holder 101, a plurality of electroencephalogram electrodes 104 are attached via respective electrode use springs 105 working as an elastic member. The respective electroencephalogram electrodes 104 are disposed at an intermediate between the mutually adjacent irradiation use optical fiber 102a and light receiving use optical fibers 102b. More specifically, the respective electroencephalogram electrodes 104 are disposed at the center or substantially at the center on the line connecting the mutually adjacent irradiation use optical fiber 102a and light receiving use optical fibers 102b. The electrode use spring 105 is compressed, when the respective electroencephalogram electrodes 104 are pressed onto the head portion of the subject. In this instance, because of the restoring force of the electrode use springs electroencephalogram electrodes 104 are pressed onto the head portion of the subject.

By mounting the holder 101 on the head portion of the subject, the irradiation use optical fibers 102a, the light receiving use optical fibers 102b and the electroencephalogram electrodes 104 are at the same time mounted on the head portion of the subject. Then in order to effect a proper measurement, contacting condition of the irradiation use optical fibers 102a, the light receiving use optical fibers 102b and the electroencephalogram electrodes 104 with the head portion of the subject is adjusted. Thereafter, inspection light is irradiated to the head portion of the subject via the irradiation use optical fibers 102a. The penetration light of the inspection light from the head portion of the subject is received by the light receiving use optical fibers 102b and sent to the main body of the living body optical measurement apparatus 300.

In the main body of the living body optical measurement apparatus 300, a physiological variation inside the living body is measured based on the penetration light sent from the light receiving use optical fibers 102b. On one hand, the output signals from the electroencephalogram electrodes 104 are sent to the main body of the brain wave measurement apparatus 400 via lead wires 113 (see FIG. 26). Thereby, in the main body of the brain wave measurement apparatus 400, the brain waves of the subject are measured.

On each of the fiber attachments 103, a fiber use reflective member 106 made of a material reflecting visible light is adhered. Further, on each of the attachment positions of the electroencephalogram electrodes 104 on the holder 101, an electrode use reflective member 107 made of a material reflecting visible light is adhered.

Through thus adhering the reflective members 106 and 107, when the holder 101 is image taken by an image taking device such as a CCD camera which can taken a two dimensional image, a mutual relative position of the fiber use reflective member 106 and the electrode use reflective member 107 is determined. Thereby, the measurement positions of the irradiation use optical fiber 102a, the light receiving use optical fibers 102b and the electroencephalogram electrodes 104 can be easily grasped without actually measuring the individual positions. Accordingly, time and work required for setting before the measurement is lightened.

Further, by image taking the holder 101 from different angles with a plurality of image taking devices, the measurement positions of the irradiation use optical fiber 102a, the light receiving use optical fibers 102b and the electroencephalogram electrodes 104 can be grasped three dimensionally.

Still further, by using such as different colors and different shapes for the fiber use reflective member 106 and the electrode use reflective member 107, both can be easily discriminated.

Still further, by using such as different colors and different shapes for the fiber use reflective member 106 corresponding to the irradiation use optical fiber 102a and the fiber use reflective member 106 corresponding to the light receiving use optical fiber 102b, both can be easily discriminated.

According to such probe device 50 used for the living body signal processing system, since the irradiation use optical fiber 102a, the light receiving use optical fibers 102b and the electroencephalogram electrodes 104 are attached on the common holder 101, both living body measurement and brain wave measurement can be performed while lightening the time and work required for setting before the measurement. Further, in the living body optical measurement apparatus 300, a brain function at the intermediate position between the irradiation use optical fiber 102a and the light receiving use optical fibers 102b is measured, and further, since in the present example, the electroencephalogram electrodes 104 is disposed at the intermediate position between the irradiation use optical fiber 102a and the light receiving use optical fibers 102b, the measurement positions by the living body optical measurement apparatus 300 and the brain wave measurement apparatus 400 can be almost met, thereby, the total measurement accuracy with the combination of the living body optical measurement apparatus 300 and the brain wave measurement apparatus 400 can be enhanced.

Further, in the present example, since the electroencephalogram electrode 104 is attached to the holder 101 via the electrode use spring 105, the electroencephalogram electrode 104 can be firmly attached to the head portion of the subject, thus the brain waves can be stably measured.

Figure 24:
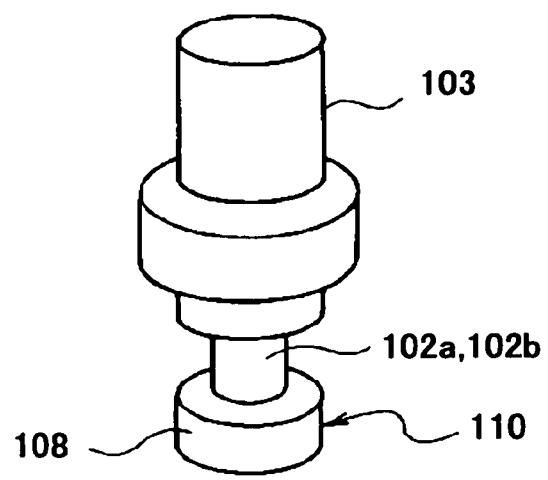
FIG. 24 is a perspective view representing an essential part of a second embodiment of a probe device used in a living body signal processing system according to the present invention.
Figure 25:
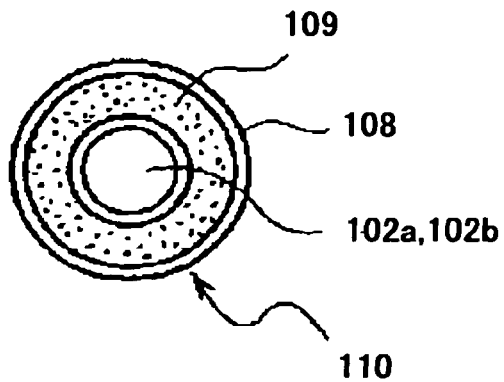
FIG. 25 is a bottom view of the top end portion of FIG. 24.

Now, FIG. 24 is a perspective view representing an essential part of another embodiment of a probe device 50 used in the living body signal processing system according to the present invention, and FIG. 25 is a bottom view of the top end portion of an optical fiber in FIG. 24. In the drawings, the top ends of the irradiation use optical fiber 102a and the light receiving use optical fibers 102b are surrounded by sleeve members 108 made of a conductive material such as copper and brass. Each of the sleeve members 108 is secured to the top ends of the respective irradiation use optical fiber 102a and light receiving use optical fibers 102b.

Between the sleeve member 108 and the respective optical fibers 102a and 102b, a liquid holding member 109 impregnated by conductive liquid is filled. As the conductive liquid, for example, physiological saline is used. As the liquid holding member 109, for example, a porous member such as sponge is used. An electroencephalogram electrode 110 is constituted by the sleeve member 108, the liquid holding member 109 and the conductive liquid held therein. Further the electroencephalogram electrodes 110 are connected to the main body of the brain wave measurement apparatus 400 via lead wires. The optical fibers 102a and 102b are attached to the holder 101 (see FIG. 23) by the fiber attachment 103.

According to such probe device 50 used for the living body signal processing system, since at the respective top ends of the living body optical measurement use optical fibers 102a and 102b, the electroencephalogram electrodes 110 is provided integrally, by contacting the optical fibers 102a and 102b to the head portion of the subject, the electroencephalogram electrodes 110 can be at the same time contacted to the head portion of the subject, the time and work required for setting before the measurement can be lightened.

Figure 26:
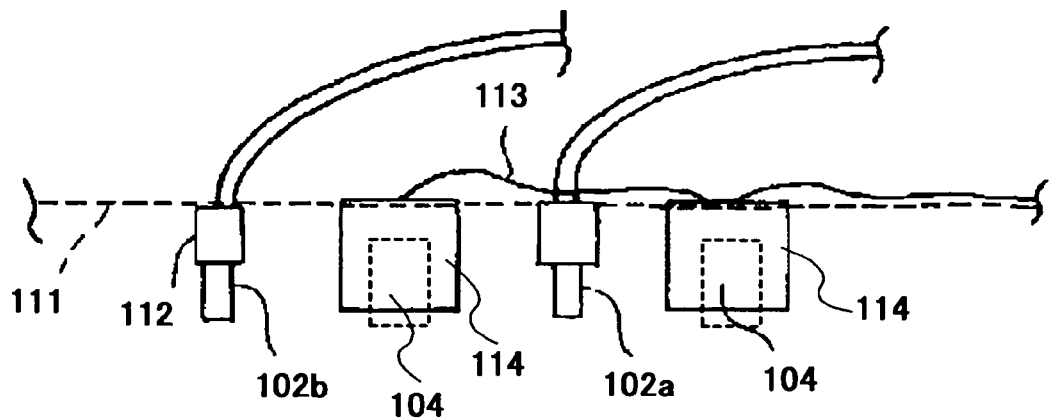
FIG. 26 is a schematic side view representing a third embodiment of a probe device used in a living body signal processing system according to the present invention.

Now, FIG. 26 is a side view representing still another embodiment of a probe device 50 used in the living body signal processing system according to the present invention. In the drawing, a net shaped holder 111 is mounted on the head portion of the subject. On the net shaped holder 111, a plurality of the irradiation use optical fibers 102a, light receiving use optical fibers 102b and electroencephalogram electrodes 104 are attached. The respective optical fibers 102a and 102b are attached to the holder 111 by the fiber attachments 112. Each of the fiber attachments 112 is provided with a slit (not shown) for passing strings. Namely, each of the fiber attachments 112 is attached to the holder 111 by passing the strings of the holder 111. Each of the electroencephalogram electrodes 104 is disposed at the intermediate position of the mutually adjacent irradiation use optical fiber 102a and light receiving use optical fibers 102b. Further, each of the electroencephalogram electrodes 104 connected to the main body of the brain wave measurement apparatus 400 via the lead wire 113.

In the probe device 50 used in the living body signal processing system, since the optical fibers 102a and 102b are designed to be attached to the strings of the holder 111 for mounting the electroencephalogram electrodes 104, both living body measurement and brain wave measurement can be performed while lightening the time and work required for setting before the measurement.

Figure 27:
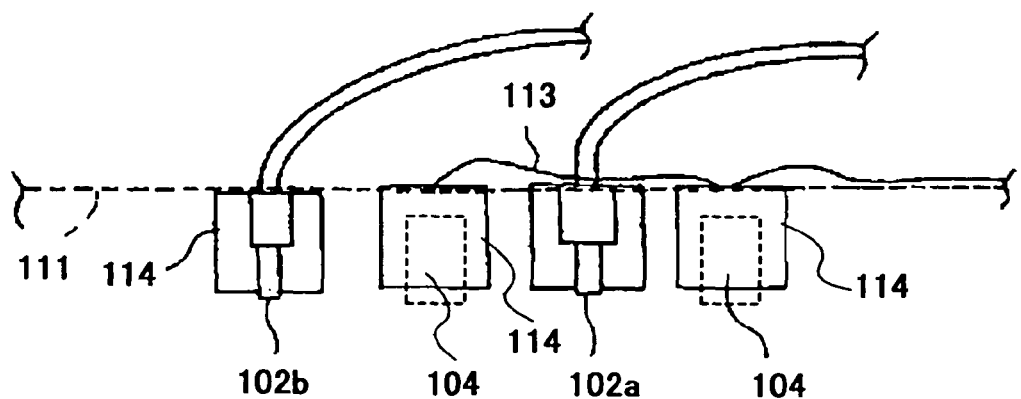
FIG. 27 is a schematic side view representing a fourth embodiment of a probe device used in a living body signal processing system according to the present invention.

Now, FIG. 27 is a side view representing a further embodiment of a probe device 50 used in the living body signal processing system according to the present invention. In the drawing, the irradiation use optical fibers 102a and the light receiving use optical fibers 102b are attached to the holder 111 by attachments 114 having the same structure as attachments 114 for the electroencephalogram electrodes 104. Accordingly, the attachment structure of the optical fibers to the holder 111 by the attachments 114 is the same as that of the electroencephalogram electrodes 104 to the holder 111.

In this manner, by equalizing the attachment structure of the electroencephalogram electrodes 104 and the optical fibers 102a and 102b to the holder 111, the entire structure can be simplified and the time and work required for setting before the measurement is lightened as well as a stable setting is effected.

Figure 28:
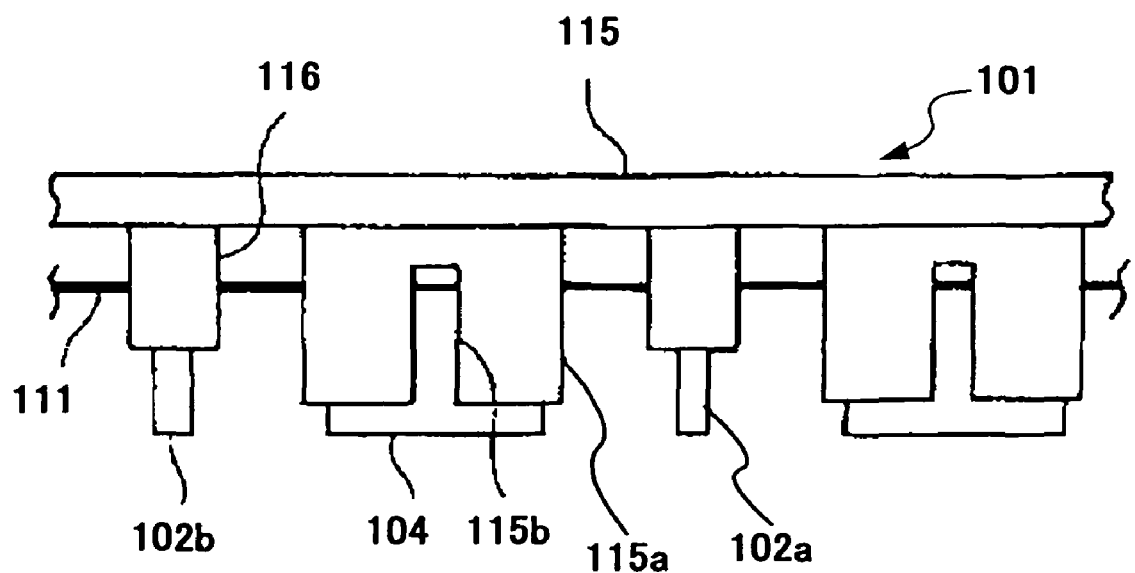
FIG. 28 is a schematic side view representing a fifth embodiment of a probe device used in a living body signal processing system according to the present invention.
Figure 29:
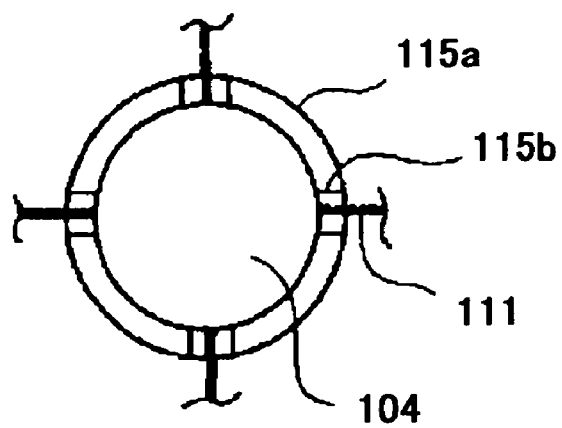
FIG. 29 is a bottom view of an essential part of the probe device of the fifth embodiment as shown in FIG. 28.

Now, FIG. 28 is a view representing a still further embodiment of a probe device 50 used in the living body signal processing system according to the present invention, and FIG. 29 is a bottom view of an essential part of the probe device as shown in FIG. 28. In the drawing, the irradiation use optical fibers 102a and the light receiving use optical fibers 102b are attached to a gel like fiber use holder (protective gel) 115 via a fiber attachment 116. The gel like fiber use holder 115 is for covering at least a part of the head portion of the subject. The electroencephalogram electrodes 104 are attached to the net shaped holder 111 working as the electrode use holder. The fiber use holder 115 is provided with, as an electrode coupling portion which couples with the electroencephalogram electrodes 104, a plurality of electrode surrounding portions 115a which surround the side portion of the electroencephalogram electrodes 104. Further, Each of the electrode surrounding portions 115a is provided with a plurality of slits for permitting escape of the strings of the net shaped holder 111.

In such probe device 50 used in the living body signal processing system, the irradiation use optical fibers 102a and the light receiving use optical fibers 102b are attached in advance to the fiber use holder 115. Further, the electroencephalogram electrodes 104 are attached to the net shaped holder 111. When disposing the optical fibers 102a and 102b and the electroencephalogram electrodes 104, at first the net shaped holder 111 is mounted on the head portion, then the fiber use holder 115 is mounted on the head portion so as to cover net shaped holder 111. At this time the electroencephalogram electrodes 104 fit into the electrode surrounding portions 115a.

In the above embodiment, since the outer circumference of the electrode use holder is covered by the gel like fiber use holder 115, when a measurement is performed under a condition where a subject lies down, and in case when the subject rolls over, a possible positional displacement of the optical fibers 102a and 102b and the electroencephalogram electrodes 104 can be prevented. In particular, with the provision of the electrode surrounding portions 115a which surround the electroencephalogram electrodes 104, not only the positional displacement of the optical fibers 102a and 102b which are directly attached to the fiber use holder 115 but also the positional displacement of the electroencephalogram electrodes 104 attached to the net shaped holder 111 can be surely prevented. Accordingly, both living body measurement and brain wave measurement can be performed at the same time while lightening the time and work required for setting before the measurement.

The invention claimed is:

1. A living body information signal processing system combining a living body optical measurement apparatus and a brain wave measurement apparatus comprising:
   the living body optical measurement apparatus in which light of from visible to near infrared is irradiated from a first position on a head portion of a subject via an irradiation use optical fiber and the penetration light is received at a second position on the head portion of the subject via a light receiving use optical fiber and which measures based on the received penetration light an optical characteristic variation induced by a brain activity inside the head portion of the subject at a measurement position corresponding to an intermediate position between the first and second positions as a living body optical signal corresponding to the measurement position;
   the brain wave measurement apparatus which measures an electrical characteristic variation induced by a brain activity inside the head portion of the subject through a brain wave electrode configured to be attached to a third position representing a measurement position on the head portion of the subject as a brain wave signal corresponding to the measurement position;
   a probe device for the living body optical measurement apparatus and the brain wave measurement apparatus which carries top end portions of the irradiation use optical fiber and the light receiving use optical fiber and the brain wave electrode and is configured to be mounted on the subject; and
   a living body information signal processing and displaying device which displays the living body optical signal corresponding to respective measurement positions from the living body optical measurement apparatus and the brain wave signal corresponding to respective measurement positions from the brain wave measurement apparatus on a common display device while correlating the respective measurement positions each other.

2. A system according to claim 1, wherein the living body information signal processing and displaying device converts the respective signal intensities of the living body optical signal and the brain wave signal corresponding to the respective measurement positions into two dimensional living body optical measurement image and brain wave measurement image expressed by shade of color and displays the same on the common display device individually or at the same time in a superposed manner or in a spatially spaced apart manner.

3. A system according to claim 2, wherein the living body information signal processing and displaying device displays at least one of the two dimensional living body optical measurement image and brain wave measurement image respectively constituted from the living body optical signal and the brain wave signal corresponding to the respective measurement positions on the common display device in an animating manner while switching the same in every unit time.

4. A system according to claim 1, wherein the living body information signal processing and displaying device displays in parallel diagrams representing time course data respectively constituted from the living body optical signal and the brain wave signal measured at a same measurement position and at a same timing on the common display device.

5. A system according to claim 4, wherein the living body information signal processing and displaying device displays the time course data at all of the measurement positions at the same time or while shifting time each other.

6. A system according to claim 1, wherein the living body information signal processing and displaying device displays the measurement positions by the living body optical measurement apparatus and by the brain wave measurement apparatus in two dimensional manner or three dimensional manner on the common display device together with an outline of a measurement portion of the subject.

7. A system according to claim 6, wherein the living body information signal processing and displaying device includes a console, permits to select a measurement position of interest among measurement positions by the living body optical measurement apparatus and by the brain wave measurement apparatus via the console and displays diagrams representing time course data of the living body optical signal and the brain wave signal of the selected measurement position on the common display device.

8. A system according to claim 1, wherein the living body information signal processing and displaying device constitutes three dimensional images from the respective intensities of the living body optical signal and the brain wave signal corresponding to the respective measurement positions while correlating the respective two dimensional positions and displays the same on the common display device as well as constitutes a third three dimensional image by synthesizing both three dimensional images mathematically and displays the same.

9. A system according to claim 1, wherein the living body information signal processing and displaying device displays diagrams representing time course data of the living body optical signal and the brain wave signal corresponding to the respective measurement positions on the common display device as well as constitutes a third diagram by synthesizing both diagrams representing time course data mathematically and displays the same.

10. A system according to claim 1, wherein the living body information signal processing and displaying device adopts or rejects the living body optical signal measured by the living body optical measurement apparatus based on the brain wave signal measured by the brain wave measurement apparatus.

11. A system according to claim 10, wherein the brain wave signal measured by the brain wave measurement apparatus is replaceable by a body motion signal measured by a body motion measurement device.

12. A system according to claim 1, wherein the living body information signal processing and displaying device includes a cooperative control unit which performs a cooperative control for sampling of the measurement data from the living body optical measurement apparatus and from the brain wave measurement apparatus.

13. A system according to claim 1, further comprising a stimulation providing device which provides stimulation to the subject, and the stimulation providing device controls stimulation to be provided based on the brain wave signal measured by the brain wave measurement apparatus.

14. A system according to claim 13, wherein the brain wave signal measured by the brain wave measurement apparatus is replaceable by a body motion signal measured by a body motion measurement device.

15. A system according to claim 1, further comprising an open eye detection device which measures an open degree of an eye of the subject, and the brain wave measurement apparatus calibrates the measured intensity of the brain wave signal depending on the open eye degree of the subject measured by the open eye detection device.

16. A system according to claim 1, wherein the top end portions of the irradiation use optical fiber and the light receiving use optical fiber and the brain wave electrode in the probe device for the living body optical measurement apparatus and the brain wave measurement apparatus are carried by a common holder.

* * * * *